(12) United States Patent
Gielen et al.

(10) Patent No.: US 9,289,270 B2
(45) Date of Patent: Mar. 22, 2016

(54) METHOD AND APPARATUS FOR PERFORMING A NAVIGATED PROCEDURE

(75) Inventors: Frans L. H. Gielen, Eckelrade (NL); Peter Appenrodt, Bremen (DE); Andrew N. Csavoy, Minneapolis, MN (US); Jeffrey M. Waynik, Nederland, CO (US); Mark S. Freas, Maplegrove, MN (US); Matthew S. Solar, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 881 days.

(21) Appl. No.: 12/626,223

(22) Filed: Nov. 25, 2009

(65) Prior Publication Data
US 2010/0160771 A1 Jun. 24, 2010

Related U.S. Application Data

(63) Continuation-in-part of application No. 12/110,666, filed on Apr. 28, 2008, which is a continuation-in-part of application No. 11/739,401, filed on Apr. 24, 2007, application No. 12/626,223, which is a continuation-in-part of application No. 11/739,424, filed on Apr. 24, 2007, now Pat. No. 8,108,025, and a continuation-in-part of application No. 12/062,605, filed on Apr. 4, 2008, now abandoned, application No. 12/626,223, which is a continuation-in-part of application No. 11/739,791, filed on Apr. 25, 2007.

(60) Provisional application No. 60/913,704, filed on Apr. 24, 2007.

(51) Int. Cl.
*A61B 5/05* (2006.01)
*A61B 19/00* (2006.01)
*A61B 17/34* (2006.01)

(52) U.S. Cl.
CPC .......... *A61B 19/5244* (2013.01); *A61B 19/201* (2013.01); *A61B 2017/3407* (2013.01); *A61B 2017/3409* (2013.01); *A61B 2019/206* (2013.01); *A61B 2019/207* (2013.01); *A61B 2019/208* (2013.01); *A61B 2019/505* (2013.01); *A61B 2019/5231* (2013.01); *A61B 2019/5251* (2013.01); *A61B 2019/5259* (2013.01); *A61B 2019/5268* (2013.01); *A61B 2019/5289* (2013.01); *A61B 2019/5483* (2013.01)

(58) Field of Classification Search
CPC .......................... A61B 19/201; A61B 19/5244
See application file for complete search history.

(56) References Cited

U.S. PATENT DOCUMENTS 5,370,118 A 12/1994 Vij et al.
5,570,182 A 10/1996 Nathel et al.
(Continued)

FOREIGN PATENT DOCUMENTS

EP 1743591 1/2007
FR 2798295 3/2001
(Continued)

OTHER PUBLICATIONS

Final Office Action mailed Apr. 13, 2011 for U.S. Appl. No. 11/739,424.
(Continued)

*Primary Examiner* — Bo J Peng
(74) *Attorney, Agent, or Firm* — Harness, Dickey & Pierce, P.L.C.

(57) ABSTRACT

A system can be used to navigate or guide an instrument or device into an anatomy of a patient. The navigation can occur with the use of image data acquired of the patient. The image data can be registered to the patient space for navigation. One or more tracking devices can be the associated with the patient and with guiding instruments for tracking guiding devices relative to the patient.

26 Claims, 11 Drawing Sheets

(56) References Cited

U.S. PATENT DOCUMENTS

| | | | |
|---|---|---|---|
| 5,577,503 A | 11/1996 | Bonutti | |
| 5,592,939 A | 1/1997 | Martinelli | |
| 5,676,673 A | 10/1997 | Ferre et al. | |
| 5,682,890 A | 11/1997 | Kormos et al. | |
| 5,740,808 A | 4/1998 | Panescu et al. | |
| 5,762,064 A | 6/1998 | Polvani | |
| 5,772,594 A | 6/1998 | Barrick | |
| 5,800,352 A * | 9/1998 | Ferre et al. | 600/407 |
| 5,868,675 A | 2/1999 | Henrion et al. | |
| 5,871,445 A | 2/1999 | Bucholz | |
| 5,913,820 A | 6/1999 | Bladen et al. | |
| 5,938,599 A | 8/1999 | Rasche et al. | |
| 5,983,126 A | 11/1999 | Wittkampf | |
| 6,006,126 A | 12/1999 | Cosman | |
| 6,011,996 A | 1/2000 | Gielen et al. | |
| 6,015,406 A | 1/2000 | Goble et al. | |
| 6,033,415 A | 3/2000 | Mittelstadt et al. | |
| 6,078,841 A | 6/2000 | Kuzma | |
| 6,084,411 A | 7/2000 | Giaquinto et al. | |
| 6,104,944 A * | 8/2000 | Martinelli | 600/424 |
| 6,106,464 A | 8/2000 | Bass et al. | |
| 6,117,143 A | 9/2000 | Hynes et al. | |
| 6,122,541 A | 9/2000 | Cosman et al. | |
| 6,195,580 B1 | 2/2001 | Grable | |
| 6,205,411 B1 | 3/2001 | DiGioia, III et al. | |
| 6,235,038 B1 | 5/2001 | Hunter et al. | |
| 6,246,900 B1 | 6/2001 | Cosman et al. | |
| 6,273,896 B1 * | 8/2001 | Franck et al. | 606/130 |
| 6,301,492 B1 | 10/2001 | Zonenshayn | |
| 6,311,082 B1 | 10/2001 | Creighton, IV et al. | |
| 6,351,662 B1 | 2/2002 | Franck et al. | |
| 6,368,329 B1 | 4/2002 | Truwit | |
| 6,381,485 B1 * | 4/2002 | Hunter | A61B 19/52 324/244 |
| 6,405,072 B1 | 6/2002 | Cosman | |
| 6,413,263 B1 | 7/2002 | Lobdill et al. | |
| 6,474,341 B1 | 11/2002 | Hunter et al. | |
| 6,477,400 B1 | 11/2002 | Barrick | |
| 6,482,182 B1 | 11/2002 | Carroll et al. | |
| 6,490,475 B1 | 12/2002 | Seeley et al. | |
| 6,491,699 B1 | 12/2002 | Henderson et al. | |
| 6,493,573 B1 | 12/2002 | Martinelli et al. | |
| 6,516,212 B1 | 2/2003 | Bladen et al. | |
| 6,529,765 B1 | 3/2003 | Franck et al. | |
| 6,546,277 B1 | 4/2003 | Franck et al. | |
| 6,606,521 B2 | 8/2003 | Paspa et al. | |
| 6,618,612 B1 | 9/2003 | Acker et al. | |
| 6,662,036 B2 | 12/2003 | Cosman | |
| 6,704,957 B2 | 3/2004 | Rhodes | |
| 6,752,812 B1 | 6/2004 | Truwit | |
| 6,826,423 B1 | 11/2004 | Hardy et al. | |
| 6,829,508 B2 | 12/2004 | Schulman et al. | |
| 6,847,849 B2 | 1/2005 | Mamo et al. | |
| 6,862,805 B1 | 3/2005 | Kuzma et al. | |
| 6,896,675 B2 | 5/2005 | Leung et al. | |
| 7,033,326 B1 | 4/2006 | Pianca et al. | |
| 7,130,676 B2 | 10/2006 | Barrick | |
| 7,177,701 B1 | 2/2007 | Pianca | |
| 7,206,627 B2 | 4/2007 | Abovitz et al. | |
| 7,217,276 B2 | 5/2007 | Henderson et al. | |
| 7,235,084 B2 | 6/2007 | Skakoon et al. | |
| 7,313,430 B2 | 12/2007 | Urquhart et al. | |
| 7,619,416 B2 | 11/2009 | Nordmeyer-Massner et al. | |
| 7,747,312 B2 | 6/2010 | Barrick et al. | |
| 7,751,865 B2 | 7/2010 | Jascob et al. | |
| 2001/0011175 A1 | 8/2001 | Hunter et al. | |
| 2001/0014820 A1 | 8/2001 | Gielen et al. | |
| 2001/0021805 A1 * | 9/2001 | Blume et al. | 600/407 |
| 2001/0034530 A1 | 10/2001 | Malackowski et al. | |
| 2002/0042619 A1 | 4/2002 | Dominguez et al. | |
| 2002/0072737 A1 | 6/2002 | Belden et al. | |
| 2002/0087101 A1 | 7/2002 | Barrick et al. | |
| 2002/0111634 A1 | 8/2002 | Stoianovici et al. | |
| 2002/0183608 A1 | 12/2002 | Marmulla et al. | |
| 2003/0009207 A1 | 1/2003 | Paspa et al. | |
| 2003/0078569 A1 | 4/2003 | Caldera et al. | |
| 2003/0097061 A1 | 5/2003 | Ferre et al. | |
| 2003/0114752 A1 | 6/2003 | Henderson et al. | |
| 2003/0163040 A1 | 8/2003 | Gildenberg | |
| 2003/0187351 A1 | 10/2003 | Franck et al. | |
| 2004/0092815 A1 | 5/2004 | Schweikard et al. | |
| 2004/0138548 A1 * | 7/2004 | Strommer et al. | 600/407 |
| 2004/0147839 A1 | 7/2004 | Moctezuma de la Barrera et al. | |
| 2004/0147851 A1 | 7/2004 | Bignall | |
| 2004/0152972 A1 * | 8/2004 | Hunter | 600/424 |
| 2004/0171924 A1 * | 9/2004 | Mire et al. | 600/407 |
| 2004/0199072 A1 | 10/2004 | Sprouse et al. | |
| 2004/0215071 A1 | 10/2004 | Frank et al. | |
| 2005/0049486 A1 * | 3/2005 | Urquhart et al. | 600/429 |
| 2005/0075649 A1 | 4/2005 | Bova et al. | |
| 2005/0085714 A1 | 4/2005 | Foley et al. | |
| 2005/0085715 A1 | 4/2005 | Dukesherer et al. | |
| 2005/0085720 A1 | 4/2005 | Jascob et al. | |
| 2005/0119587 A1 | 6/2005 | Roessler et al. | |
| 2005/0198849 A1 | 9/2005 | Goeggelmann et al. | |
| 2005/0226377 A1 | 10/2005 | Wong et al. | |
| 2006/0058683 A1 | 3/2006 | Chance | |
| 2006/0190054 A1 | 8/2006 | Malinowski et al. | |
| 2006/0212044 A1 | 9/2006 | Bova et al. | |
| 2006/0241406 A1 | 10/2006 | Noujeim | |
| 2006/0253181 A1 | 11/2006 | Schulman et al. | |
| 2007/0015991 A1 | 1/2007 | Fu et al. | |
| 2007/0027385 A1 | 2/2007 | Brister et al. | |
| 2007/0167722 A1 | 7/2007 | Bladen et al. | |
| 2008/0204021 A1 | 8/2008 | Leussler et al. | |
| 2008/0269599 A1 | 10/2008 | Csavoy et al. | |
| 2008/0269600 A1 | 10/2008 | Csavoy et al. | |
| 2008/0269602 A1 | 10/2008 | Csavoy et al. | |
| 2008/0269777 A1 | 10/2008 | Appenrodt et al. | |
| 2009/0012509 A1 | 1/2009 | Csavoy et al. | |
| 2009/0261828 A1 | 10/2009 | Nordmeyer-Massner et al. | |

FOREIGN PATENT DOCUMENTS

| | | |
|---|---|---|
| GB | 2352512 | 1/2001 |
| WO | WO-9608209 | 3/1996 |
| WO | WO-9611624 A2 | 4/1996 |
| WO | WO-9833451 | 8/1998 |
| WO | WO-0050859 | 8/2000 |
| WO | WO-0224094 | 3/2002 |
| WO | WO-2004044612 | 5/2004 |
| WO | WO-2004100767 | 11/2004 |
| WO | WO-2005039386 | 5/2005 |
| WO | WO-2007002926 | 1/2007 |
| WO | WO-2008036050 | 3/2008 |

OTHER PUBLICATIONS

Final Office Action mailed Feb. 11, 2011 for U.S. Appl. No. 12/110,666.

Interview Summary mailed Feb. 2, 2011 for U.S. Appl. No. 11/739,424.

Notice of Allowance mailed Jun. 9, 2011 for U.S. Appl. No. 11/739,401.

Notice of Allowance mailed May 12, 2011 for U.S. Appl. No. 12/110,666.

Office Action mailed May 11, 2011 for U.S. Appl. No. 12/062,605.

Final Office Action mailed Oct. 14, 2011 for U.S. Appl. No. 12/062,605.

Interview Summary mailed Aug. 18, 2011 for U.S. Appl. No. 12/062,605.

Notice of Allowance mailed Sep. 14, 2011 for U.S. Appl. No. 11/739,424.

Office Communication and Issue Classification mailed Oct. 7, 2011 for U.S. Appl. No. 11/739,424.

"3M Surgical Drapes, Drape Selection Guide," brochure, 3M copyright 2002, 2003, 2005.

"Fazer® Contour Laser," 9730732, rev. 3 8/06. 9 Sheets.

"MicroTargeting Drive System for Stereotactice Positioning" FHC, Inc., Mar. 2006.

"MicroTargeting® Drive System for Stereotactic Positioning," User Manual L011-1006B, Mar. 2006.

(56) References Cited

OTHER PUBLICATIONS

"Navigus, NexFrame, StimLoc", IGN—Image Guided Neurologics, copyright 2004, printed from www.igneurologics.com on Jul. 9, 2007, (2 sheets).
"NeuroNav™," *Alpha Omega Defining Neuroscience Technology*, http://www.alphaomega-eng.com/pr_site/neuronav/index.htm, Web. accessed Apr. 1, 2010.
"NexDrive™ Micro-Positioner, Microelectrode Recording & DBS™ Electrode Implantation," Medtronic, Inc. copyright 2006. (2 sheets).
"Nexframe Reticle System, Trajectory Orientation," Medtronic, Inc. copyright 2006. (2 sheets).
"NexFrame System—Case: Bilateral Activa Lead Delivery to STN Using Nexframe," IGN Image Guided Neurologics, Inc. copyright 2004. Printed from www.igneurologics.com on Jul. 9, 2007. (2 sheets).
"Nexframe," 2 sheets printed from www.igneurologics.com on Jul. 9, 2007.
"Passive Headrest, Full Head and Neck Support," Medtronic, Inc. copyright 2006, (2 sheets).
"Stimloc™ Lead Securement Device," Medtronic, Inc. 2006. (2 sheets).
"The DBS Solution, Enabling Technologies, Case Studies," Medtronic, Inc. copyright 2006.
"The NexFrame System, Stereotactic Technology," Medtronic, Inc. copyright 2006. (3 sheets).
"Tracer™ Registration Feature", 9731369, rev. 2 Sep. 2004. 3 sheets.
"Unibody™ Fiducials, Unibody Fiducial Marker," Medtronic, Inc. copyright 2006, (2 sheets).
Communication Relating to the Results of the Partial International Search for PCT/US2007/010164 included as part of Invitation to Pay Additional Fees mailed Feb. 21, 2008.
International Preliminary Report on Patentability and Written Opinion for PCT/US2007/009928 mailed Nov. 5, 2009 claiming benefit of U.S. Appl. No. 11/739,401, filed Apr. 24, 2007.
International Preliminary Report on Patentability and Written Opinion for PCT/US2007/010121 issued Oct. 27, 2009 claiming benefit of U.S. Appl. No. 11/739,424, filed Apr. 24, 2007.
International Preliminary Report on Patentability and Written Opinion for PCT/US2007/010164 mailed Nov. 5, 2009 claiming benefit of U.S. Appl. No. 11/739,791, filed Apr. 25, 2007.
International Search Report and Written Opinion for case PCT/US2008/060316 mailed Jul. 11, 2008.
International Search Report and Written Opinion for PCT/US2007/009928 mailed on Mar. 26, 2008.
International Search Report and Written Opinion for PCT/US2007/010121 mailed Jan. 24, 2008.
International Search Report and Written Opinion for PCT/US2007/010164 mailed May 30, 2008 claiming benefit of U.S. Appl. No. 11/739,791, filed Apr. 25, 2007.
International Search Report and Written Opinion for PCT/US2008/082961 mailed Mar. 3, 2009 claiming benefit of U.S. Appl. No. 12/110,666, filed Apr. 28, 2008, which claims priority to U.S. Appl. No. 11/739,401, filed Apr. 24, 2007.
Johnson, Jennie et al., "Independently movable multielectrode array to record multiple fast-spiking neurons in the cerebral cortex during cognition" Methods, vol. 30, 2003, pp. 64-78, XP002465099 sections 2.2., 3.2; figures 1,2.
Rosenow, Joshua, "Application Accuracy of an Electromagnetic Field-Based Image-Guided Navigation System," Stereotactic Fuct Neurosurg 2007; 85:75-81, Dec. 12, 2006.
Final Office Action mailed Dec. 3, 2010 for U.S. Appl. No. 11/739,401.
Office Action mailed Aug. 19, 2010 for U.S. Appl. No. 11/739,401.
Restriction Requirement mailed Jul. 19, 2010 for U.S. Appl. No. 12/110,666.
Office Action mailed Sep. 15, 2010 for U.S. Appl. No. 12/110,666.
Office Action mailed Oct. 27, 2010 for U.S. Appl. No. 11/739,424.

* cited by examiner

METHOD AND APPARATUS FOR PERFORMING A NAVIGATED PROCEDURE

CROSS-REFERENCE TO RELATED APPLICATIONS

This application is a continuation-in-part of U.S. patent application Ser. No. 12/110,666 filed on Apr. 28, 2008, entitled "METHOD AND APPARATUS FOR PERFORMING A NAVIGATED PROCEDURE"; which is a continuation-in-part of U.S. patent application Ser. No. 11/739,401 filed on Apr. 24, 2007, entitled, "METHOD FOR PERFORMING MULTIPLE REGISTRATIONS IN A NAVIGATED PROCEDURE." The disclosures of all of the above applications are incorporated herein by reference.

This application is also a continuation-in-part of U.S. patent application Ser. No. 11/739,424, filed Apr. 24, 2007, entitled "FLEXIBLE ARRAY FOR USE IN NAVIGATED SURGERY. The disclosure of the above application is incorporated herein by reference.

This application is also a continuation-in-part of U.S. patent application Ser. No. 12/062,605, filed Apr. 4, 2008, entitled "NAVIGATED SOFT TISSUE PENETRATING LASER SYSTEM"; which claims benefit of provisional U.S. Pat. App. No. 60/913,704, filed Apr. 24, 2007. The disclosures of all of the above applications are incorporated herein by reference.

This application is also a continuation-in-part of U.S. patent application Ser. No. 11/739,791, filed Apr. 25, 2007, entitled "METHOD AND APPARATUS FOR CONTROLLED INSERTION AND WITHDRAWAL OF ELECTRODES." The disclosure of the above application is incorporated herein by reference.

FIELD

The present disclosure relates to a surgical navigation system, and particularly to a method and apparatus for navigating instruments.

BACKGROUND

The statements in this section merely provide background information related to the present disclosure and may not constitute prior art.

In an anatomy, such as a human anatomy, various anatomical portions and functions maybe damaged or require repair after a period of time. The anatomical portion or function maybe injured due to wear, aging, disease, or exterior trauma. To assist the patient, a procedure may be performed that may require access to an internal region of the patient through an incision. Due to exterior soft tissue, visualization of portions of the interior of the anatomy maybe difficult or require a large opening in the patient.

Image data maybe required of a patient to assist in planning, performing, and post operative analysis of a procedure. For example, magnetic resonance image data can be acquired of the patient to assist in diagnosing and planning a procedure. The image data acquired of the patient can also be used to assist in navigating various instruments relative to the patient while performing a procedure.

It is known to fixedly interconnect fiducial markers with a patient while imaging the patient and substantially using the fiducial markers that are imaged in the image data to correlate or register the image data to patient space. The fiducial markers, to ensure maximum reliability, however, are generally fixed directly to a bone of the patient. It is desirable, in various procedures, to substantially minimize or eliminate the invasiveness of inserting the fiducial markers into the bone through the skin of the patient. It is also desirable to provide an efficient mechanism to allow for registration of the image space to the physical space without requiring a separate procedure to implant one or more fiducial markers. It is also desirable to provide a system that allows for registration of the image space to the patient space without requiring a user to touch or contact one or more fiducial markers on a patient.

SUMMARY

During a surgical procedure on an anatomy, such as a human anatomy, instruments, implants, prosthesis, leads, electrodes and the like can be positioned in the anatomy. The various instruments or devices are generally positioned through incisions formed in soft tissue and/or hard tissue, such as the dermis and the cranium, of the anatomy. Therefore, anatomy of the patient can obscure or limit visualization of the devices in the anatomy during the procedure. It may be desirable, therefore, to provide a mechanism to determine a position of the devices within the anatomy.

According to various embodiments, a system to register image space to physical space of a patient for a surgical navigation procedure is disclosed. The system can include a first dynamic reference frame that can be attached relative to the patient in a first manner and a second dynamic reference frame that can be attached to the patient in a second manner. A tracked device can be used to determine a fiducial point on the patient. A processor can correlate the fiducial point on the patient to an image fiducial point in the image data. A tracking system can track at least one of the tracked devices, the first dynamic reference frame, the second dynamic reference frame, or combinations thereof. The processor can register the image space and physical space with the first dynamic reference frame with a first accuracy and can register the image space and physical space with the second dynamic reference frame with a second accuracy.

According to various embodiments, a method to register image space to physical space of a patient for a surgical navigation procedure is taught. The method can include acquiring image data of the patient defining the image space and including an image fiducial point and identifying the image fiducial point in the image data. A first dynamic reference frame can be attached to the patient in a first manner and a first registration of the image space to the physical space having a first accuracy can be performed with the attached first dynamic reference frame. A second dynamic reference frame can be attached to the patient in a second manner and a second registration of the image space to the physical space having a second accuracy can be performed with the attached second dynamic reference frame.

According to various embodiments, a method to register image space to physical space of a patient for a surgical navigation procedure is disclosed. The method can include attaching a fiducial marker with the patient and acquiring image data of the patient including an image fiducial point produced by the fiducial marker. The method can also include non-invasively attaching a first dynamic reference frame to the patient in a first manner, performing a first registration of the image data to the physical space having a first accuracy with the attached first dynamic reference frame, and navigating a first procedure with the performed first registration. The method can further include invasively attaching a second dynamic reference frame to the patient in a second manner, performing a second registration of the image data to the physical space having a second accuracy with the connected second dynamic reference frame, and navigating a second procedure with the performed second registration.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Although the following description illustrates and describes a procedure relative to a cranium of a patient, the current disclosure is not to be understood to be limited to such a procedure. For example, a procedure can also be performed relative to a spinal column, heart, vascular system, etc. Therefore, discussion herein relating to a specific region of the anatomy will be understood to be applicable to all regions of the anatomy, unless specifically described otherwise.

As discussed herein various systems and elements can be used to assist in a surgical procedure. For example, image data can be acquired of a patient to assist in illustrating the location of an instrument relative to a patient. Generally, image space can be registered to patient space to assist in this display and navigation. Fiducial markers can be affixed to the patient during imaging and registration or fiducial marker-less systems can be used. Fiducial marker-less systems can use other techniques, including surface or contour matching, as discussed herein. Various techniques can be used in fiducial marker-less systems, including, but not limited to, soft tissue penetrating laser systems, flexible members including tracking devices, etc. Also, procedures can include two registration procedures, including a course and a fine registration. The two registrations can allow for lessoning invasiveness of the procedure and increasing efficiency of the procedure.

Figure 1:
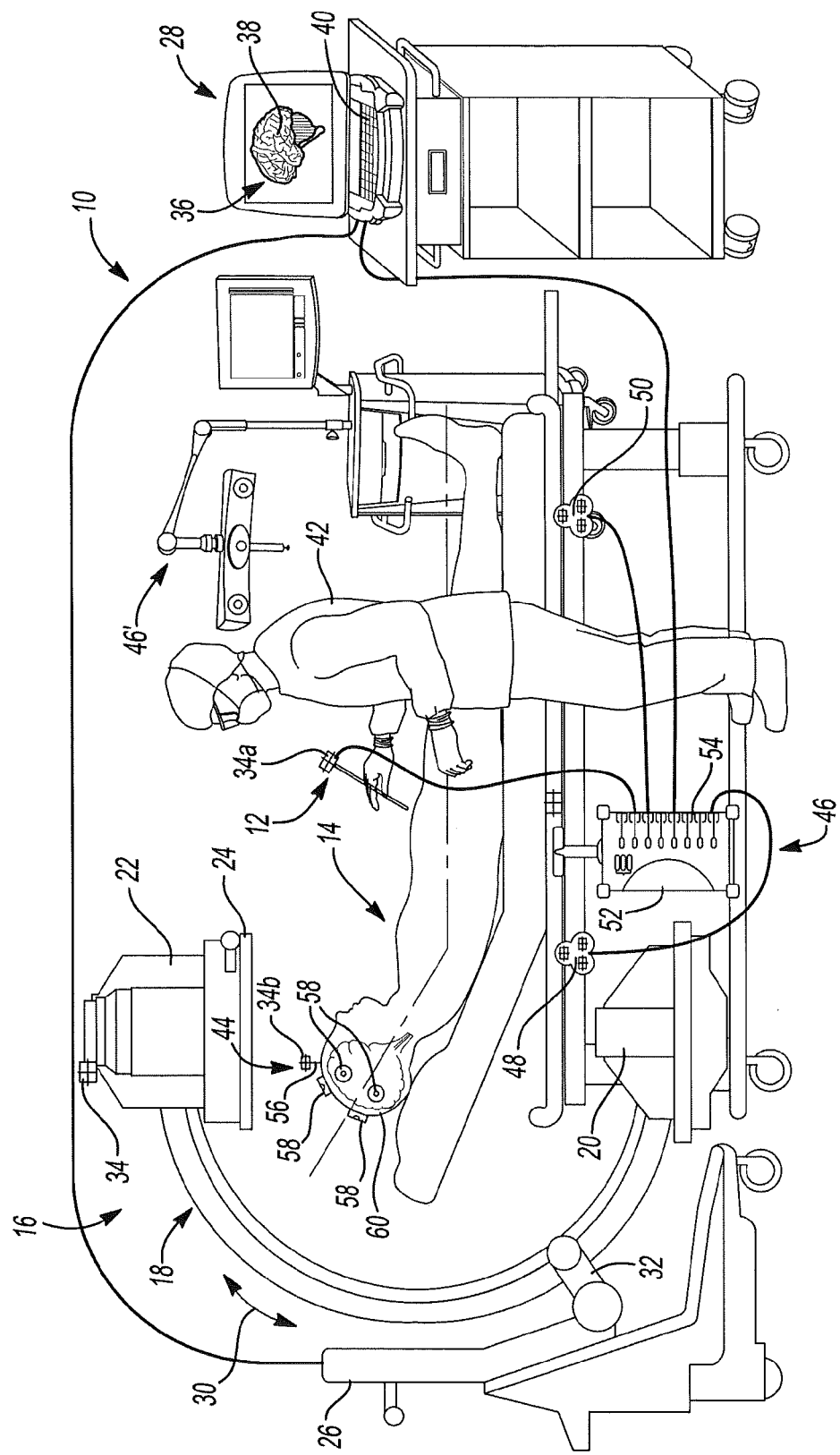
FIG. 1 is an environmental view of a surgical navigation system or computer aided surgical system, according to various embodiments.

With reference to FIG. 1, a navigation system 10 that can be used for various procedures is illustrated. The navigation system 10 can be used to track the location of a device 12, such as a pointer probe, relative to a patient 14 to assist in the implementation or performance of a surgical procedure. It should be further noted that the navigation system 10 may be used to navigate or track other devices including: catheters, probes, needles, leads, electrodes implants, etc. According to various embodiments, examples include ablation catheters, deep brain stimulation (DBS) leads or electrodes, microelectrode (ME) leads or electrodes for recording, etc. Moreover, the navigated device may be used in any region of the body. The navigation system 10 and the various devices may be used in any appropriate procedure, such as one that is generally minimally invasive, arthroscopic, percutaneous, stereotactic, or an open procedure. Although an exemplary navigation system 10 including an imaging system 16 are discussed herein, one skilled in the art will understand that the disclosure is merely for clarity of the present discussion and any appropriate imaging system, navigation system, patient specific data, and non-patient specific data can be used. For example, the intraoperative imaging system can include an MRI imaging system, such as the PoleStar® MRI imaging system or an O-arm® imaging system sold by Medtronic, Inc. having a place of business in Minnesota, USA. It will be understood that the navigation system 10 can incorporate or be used with any appropriate preoperatively or intraoperatively acquired image data.

The navigation system 10 can include the optional imaging device 16 that is used to acquire pre-, intra-, or post-operative, including real-time, image data of the patient 14. In addition, data from atlas models can be used to produce images for navigation, though they may not be patient images. Although, atlas models can be morphed or changed based upon patient specific information. Also, substantially imageless systems can be used, such as those disclosed in U.S. patent application Ser. No. 10/687,539, filed Oct. 16, 2003, now U.S. Pat. App. Pub. No. 2005/0085714, entitled "METHOD AND APPARATUS FOR SURGICAL NAVIGATION OF A MULTIPLE PIECE CONSTRUCT FOR IMPLANTATION", incorporated herein by reference. Various systems can use data based on determination of the position of various elements represented by geometric shapes.

The optional imaging device 16 is, for example, a fluoroscopic X-ray imaging device that may be configured as a C-arm 18 having an X-ray source 20, an X-ray receiving section 22, an optional calibration and tracking target 24 and optional radiation sensors. The calibration and tracking target 24 includes calibration markers (not illustrated). Image data may also be acquired using other imaging devices, such as those discussed above and herein.

An optional imaging device controller 26 may control the imaging device 16, such as the C-arm 18, which can capture the X-ray images received at the receiving section 22 and store the images for later use. The controller 26 may also be separate from the C-arm 18 and can be part of or incorporated into a work station 28. The controller 26 can control the rotation of the C-arm 18. For example, the C-arm 18 can move in the direction of arrow 30 or rotate about a longitudinal axis 14a of the patient 14, allowing anterior or lateral views of the patient 14 to be imaged. Each of these movements involves rotation about a mechanical axis 32 of the C-arm 18. The movements of the imaging device 16, such as the C-arm 18 can be tracked with a tracking device 34. As discussed herein, the tracking device, according to various embodiments, can be any appropriate tracking device to work with any appropriate tracking system (e.g. optical, electromagnetic, acoustic, etc.). Therefore, unless specifically discussed otherwise, the tracking device can be any appropriate tracking device.

In the example of FIG. 1, the longitudinal axis 14a of the patient 14 is substantially in line with the mechanical axis 32 of the C-arm 18. This enables the C-arm 18 to be rotated relative to the patient 14, allowing images of the patient 14 to be taken from multiple directions or in multiple planes. An example of a fluoroscopic C-arm X-ray device that may be used as the optional imaging device 16 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling mounted fluoroscopic systems, cath-lab fluoroscopic systems, fixed C-arm fluoroscopic systems, isocentric C-arm fluoroscopic systems, three-dimensional (3D) fluoroscopic systems, intraoperative O-arm™ imaging systems, etc.

The C-arm imaging system 18 can be any appropriate system, such as a digital or CCD camera, which are well understood in the art. Two dimensional fluoroscopic images that may be taken by the imaging device 16 are captured and stored in the C-arm controller 26. Multiple two-dimensional images taken by the imaging device 16 may also be captured and assembled to provide a larger view or image of a whole region of the patient 14, as opposed to being directed to only a portion of a region of the patient. For example, multiple image data or sets of data of a patient's leg, cranium, and brain may be appended together to provide a full view or complete set of image data of the leg or brain that can be later used to follow contrast agent, such as bolus or therapy tracking. The multiple image data can include multiple two-dimensional (2D) slices that are assembled into a 3D model or image.

The image data can then be forwarded from the C-arm controller 26 to the navigation computer and/or processor controller or work station 28 having a display device 36 to display image data 38 and a user interface 40. The work station 28 can also include or be connected to an image processor, a navigation processor, and a memory to hold instruction and data. The work station 28 can also include an optimization processor that assists in a navigated procedure. It will also be understood that the image data is not necessarily first retained in the controller 26, but may also be directly transmitted to the workstation 28. Moreover, processing for the navigation system and optimization can all be done with a single or multiple processors all of which may or may not be included in the workstation 28.

The work station 28 provides facilities for displaying the image data 38 as an image on the display device 36, saving, digitally manipulating, or printing a hard copy image of the received image data. The user interface 40, which may be a keyboard, mouse, touch pen, touch screen or other suitable device, allows a physician or user 42 to provide inputs to control the imaging device 16, via the C-arm controller 26, or adjust the display settings of the display 36. The work station 28 may also direct the C-arm controller 26 to adjust the rotational axis 32 of the C-arm 18 to obtain various two-dimensional images in different planes in order to generate representative two-dimensional and three-dimensional images.

While the optional imaging device 16 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference). Intra-vascular ultrasound (IVUS), intra-operative CT, single photo emission computed tomography (SPECT), planar gamma scintigraphy (PGS). Addition imaging systems include intraoperative MRI systems such as the PoleStar® MRI imaging system. Further systems include the O-Arm® imaging system. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 16, as shown in FIG. 1, provides a virtual bi-plane image using a single-head C-arm fluoroscope as the optional imaging device 16 by simply rotating the C-arm 18 about at least two planes, which could be orthogonal planes to generate two-dimensional images that can be converted to three-dimensional volumetric images. By acquiring image data in more than one plane, an icon representing the location of an impacter, stylet, reamer driver, taps, drill, DBS electrodes, ME electrodes for recording, probe, or other instrument, introduced and advanced in the patient 14, may be superimposed in more than one view on display 36 allowing simulated bi-plane or even multi-plane views, including two and three-dimensional views.

Four-dimensional (4D) image information can be used with the navigation system 10 as well. For example, the user 42 can use a physiologic signal, which can include Heart Rate (measured with an EKG), Breath Rate (Breath Gating) and combine this data with image data 38 acquired during the phases of the physiologic signal to represent the anatomy of the patient 14 at various stages of the physiologic cycle. For example, with each heartbeat the brain pulses (and therefore moves). Images can be acquired to create a 4D map of the brain, onto which atlas data and representations of a device, such as a surgical instrument can be projected. This 4D data set can be matched and co-registered with the physiologic signal (e.g. EKG) to represent a compensated image within the system. The image data registered with the 4D information can show the brain (or anatomy of interest) moving during the cardiac or breath cycle. This movement can be displayed on the display 36 as the image data 38. Also, the gating techniques can be used to eliminate movement in the image displayed on the display device 36.

Likewise, other imaging modalities can be used to gather the 4D dataset to which pre-operative 2D and 3D data can be matched. One need not necessarily acquire multiple 2D or 3D images during the physiologic cycle of interest (breath or heart beat). Ultrasound imaging or other 4D imaging modalities can be used to create an image data that allows for a singular static pre-operative image to be matched via image-fusion techniques and/or matching algorithms that are non-linear to match the distortion of anatomy based on the movements during the physiologic cycle. The combination of a dynamic reference frame 44 and 4D registration techniques can help compensate for anatomic distortions during movements of the anatomy associated with normal physiologic processes.

With continuing reference to FIG. 1, the navigation system 10 can further include a tracking system, such as, but not limited to, an electromagnetic (EM) tracking system 46 or an optical tracking system 46'. Either or both can be used alone or together in the navigation system 10. Moreover, discussion of the EM tracking system 46 can be understood to relate to any appropriate tracking system. The optical tracking system 46' can include the Stealthstation® Treatment Guidance System including the Treon® Navigation System and the Tria® Navigation System, both sold by Medtronic Navigation, Inc. Other tracking systems include acoustic, radiation, radar, infrared, etc.

The EM tracking system 46 includes a localizer, such as a coil array 48 and/or second coil array 50, a coil array controller 52, a navigation probe interface 54, a device 12 (e.g. catheter, needle, pointer probe, or instruments, as discussed herein) and the dynamic reference frame 44. An instrument tracking device 34a can also be associated with, such as fixed to, the instrument 12 or a guiding device for an instrument. The dynamic reference frame 44 can include a dynamic reference frame holder 56 and a removable tracking device 34b. Alternatively, the dynamic reference frame 44 can include the tracking device 34b that can be formed integrally or separately from the DRF holder 56.

Moreover, the DRF 44 can be provided as separate pieces and can be positioned at any appropriate position on the anatomy. For example, the tracking device 34b of the DRF can be fixed to the skin of the patient 14 with an adhesive. Also, the DRF 44 can be positioned near a leg, arm, etc. of the patient 14. Thus, the DRF 44 does not need to be provided with a head frame or require any specific base or holding portion.

The tracking devices 34, 34a, 34b or any tracking device as discussed herein, can include a sensor, a transmitter, or combinations thereof. Further, the tracking devices can be wired or wireless to provide a signal emitter or receiver within the navigation system. For example, the tracking device can include an electromagnetic coil to sense a field produced by the localizing array 48, 50. The EM tracking devices can include one or more coil, such as a tri-axial coil array. Optical tracking device can include one or more reflectors that can reflect a signal to be received by the optical tracking system 46'. The optical tracking devices can also actively emit or be powered to emit optical energy to be sensed with the optical tracking system 46' Nevertheless, one will understand that the tracking device can receive a signal, transmit a signal, or combinations thereof to provide information to the navigation system 10 to determine a location of the tracking device 34, 34a, 34b. The navigation system 10 can then determine a position of the instrument or tracking device to allow for navigation relative to the patient and patient space.

The coil arrays 48, 50 may also be supplemented or replaced with a mobile localizer. The mobile localizer may be one such as that described in U.S. patent application Ser. No. 10/941,782, filed Sep. 15, 2004, now U.S. Pat. App. Pub. No. 2005/0085720, entitled "METHOD AND APPARATUS FOR SURGICAL NAVIGATION", herein incorporated by reference. As is understood the localizer array can transmit signals that are received by the tracking devices 34, 34a, 34b. The tracking devices 34, 34a, 34b can then transmit or receive signals based upon the transmitted or received signals from or to the array 48, 50.

Further included in the navigation system 10 may be an isolator circuit or assembly (not illustrated separately). The isolator circuit or assembly may be included in a transmission line to interrupt a line carrying a signal or a voltage to the navigation probe interface 54. Alternatively, the isolator circuit included in the isolator box may be included in the navigation probe interface 80, the device 12, the dynamic reference frame 44, the transmission lines coupling the devices, or any other appropriate location. The isolator assembly is operable to isolate any of the instruments or patient coincidence instruments or portions that are in contact with the patient should an undesirable electrical surge or voltage take place.

It should further be noted that the entire tracking system 46, 46' or parts of the tracking system 46, 46' may be incorporated into the imaging device 16, including the work station 28. Incorporating the tracking system 46, 46' may provide an integrated imaging and tracking system. This can be particularly useful in creating a fiducial-less system. Moreover, fiducial marker-less systems can include a tracking device and a contour determining system, including those discussed herein. Any combination of these components may also be incorporated into the imaging system 16, which again can include a fluoroscopic C-arm imaging device or any other appropriate imaging device.

The EM tracking system 46 uses the coil arrays 48, 50 to create an electromagnetic field used for navigation. The coil arrays 48, 50 can include a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 48 is controlled or driven by the coil array controller 52. The coil array controller 52 drives each coil in the coil array 48 in a time division multiplex or a frequency division multiplex manner. In this regard, each coil may be driven separately at a distinct time or all of the coils may be driven simultaneously with each being driven by a different frequency.

Upon driving the coils in the coil array 48 with the coil array controller 52, electromagnetic fields are generated within the patient 14 in the area where the medical procedure is being performed, which is again sometimes referred to as patient space. The electromagnetic fields generated in the patient space induce currents in the tracking device 34, 34a, 34b positioned on or in the device 12, DRF 44, etc. These induced signals from the tracking devices 34, 34a, 34b are delivered to the navigation probe interface 54 and subsequently forwarded to the coil array controller 52. The navigation probe interface 54 can also include amplifiers, filters and buffers to directly interface with the tracking device 34b attached to the device 12. Alternatively, the tracking device 34b, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 54.

Various portions of the navigation system 10, such as the device 12, the dynamic reference frame 44, are equipped with at least one, and generally multiple, EM or other tracking devices 34a, 34b, that may also be referred to as localization sensors. The EM tracking devices 34a, 34b can include one or more coils that are operable with the EM localizer arrays 48, 50. An alternative tracking device may include an optical device, and may be used in addition to or in place of the electromagnetic tracking devices 34a, 34b. The optical tacking device may work with the optional optical tracking system 46'. One skilled in the art will understand, however, that any appropriate tracking device can be used in the navigation system 10. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

In brief, the EM tracking device 34a on the device 12 can be in a handle or inserter that interconnects with an attachment and may assist in placing an implant or in driving a member. The device 12 can include a graspable or manipulable portion at a proximal end and the tracking device 34b may be fixed near the manipulable portion of the device 12 or at a distal working end, as discussed herein. The tracking device 34a can include an electromagnetic tracking sensor to sense the electromagnetic field generated by the coil array 48, 50 that can induce a current in the electromagnetic device 34a. Alternatively, the tracking device 34a can be driven (i.e., like the coil array above) and the tracking array 48, 50 can receive a signal produced by the tracking device 34a.

The dynamic reference frame 44 may be fixed to the patient 14 adjacent to the region being navigated so that any movement of the patient 14 is detected as relative motion between the coil array 48, 50 and the dynamic reference frame 44. The dynamic reference frame 44 can be interconnected with the patient in any appropriate manner, including those discussed herein. Relative motion is forwarded to the coil array controller 52, which updates registration correlation and maintains accurate navigation, further discussed herein. The dynamic reference frame 44 may include any appropriate tracking device. Therefore, the dynamic reference frame 44 may also be EM, optical, acoustic, etc. If the dynamic reference frame 44 is electromagnetic it can be configured as a pair of orthogonally oriented coils, each having the same center or may be configured in any other non-coaxial or co-axial coil configurations.

Briefly, the navigation system 10 operates as follows. The navigation system 10 creates a translation map between all points in the image data generated from the imaging device 16 which can include external and internal portions, and the corresponding points in the patient's anatomy in patient space. After this map is established, whenever the tracked device 12 is used, the work station 36 in combination with the coil array controller 52 uses the translation map to identify the corresponding point on the image data or atlas model, which is displayed on display 36. This identification is known as navigation or localization. An icon representing the localized point or instruments is shown on the display 36 within several two-dimensional image planes, as well as on three and four dimensional images and models.

To enable navigation, the navigation system 10 must be able to detect both the position of the patient's anatomy and the position of the instrument 12 or an attachment member (e.g. tracking device 34a) attached to the instrument 12. Knowing the location of these two items allows the navigation system 10 to compute and display the position of the instrument 12 or any portion thereof in relation to the patient 14. The tracking system 46 is employed to track the instrument 12 and the anatomy of the patient 14 simultaneously.

The tracking system 46, if it is using an electromagnetic tracking assembly, essentially works by positioning the coil array 48, 50 adjacent to the patient 14 to generate a magnetic field, which can be low energy, and generally referred to as a navigation field. Because every point in the navigation field or patient space is associated with a unique field strength, the electromagnetic tracking system 46 can determine the position of the instrument 12 by measuring the field strength at the tracking device 34a location. The dynamic reference frame 44 is fixed to the patient 14 to identify the location of the patient in the navigation field. The electromagnetic tracking system 46 continuously computes or calculates the relative position of the dynamic reference frame 44 and the instrument 12 during localization and relates this spatial information to patient registration data to enable navigation of the device 12 within and/or relative to the patient 14. Navigation can include image guidance or imageless guidance.

Patient registration is the process of determining how to correlate the position of the instrument 12 relative to the patient 14 to the position on the diagnostic or image data. To register the patient 14, the physician or user 42 may select and store one or more particular points from the image data and then determine corresponding points on the patient's anatomy, such as with the pointer probe 12. The navigation system 10 analyzes the relationship between the two sets of points that are selected and computes a match, which correlates every point in the image data with its corresponding point on the patient's anatomy or the patient space.

The points that are selected to perform registration can be image fiducial points. The image fiducial points can be produced by a fiducial marker 58 or selected landmarks, such as anatomical landmarks. The landmarks or fiducial markers 58 are identifiable in the image data and identifiable and accessible on the patient 14. The anatomical landmarks can include individual or distinct points on the patient 14 or contours (e.g. three-dimensional contours) defined by the patient 14. The fiducial markers 58 can be artificial markers that are positioned on the patient 14. The artificial landmarks, such as the fiducial markers 58, can also form part of the dynamic reference frame 44, such as those disclosed in U.S. Pat. No. 6,381,485, entitled "Registration of Human Anatomy Integrated for Electromagnetic Localization," issued Apr. 30, 2002, herein incorporated by reference. Various fiducial marker-less systems, including those discussed herein, may not include the fiducial markers 58, or other artificial markers. The fiducial marker-less systems include a device or system to define in the physical space the landmark or fiducial points on the patient or contour on the patient. A fiducialless and markerless system can include those that do not include artificial or separate fiducial markers that are attached to or positioned on the patient 14.

As discussed above, registration of the patient space or physical space to the image data or image space can require the correlation or matching of physical or virtual fiducial points and image fiducial points. The physical fiducial points can be the fiducial markers 60 or landmarks (e.g. anatomical landmarks) in the substantially fiducial marker-less systems.

The registration can require the determination of the position of physical fiducial points. The physical fiducial points can include the fiducial markers 58. The user 42 can touch the fiducial markers or devices 58 on the patient 14 or a tracking device can be associated with the fiducial markers 58 so that the tracking system 46, 46' can determine the location of the fiducial markers 58 without a separate tracked device. The physical fiducial points can also include a determined contour (e.g. a physical space 3d contour) using various techniques, as discussed herein.

The image fiducial points in the image data 54 can also be determined. The user 42 can touch or locate the image fiducial points, either produced by imaging of the fiducial markers 48 or the landmarks. Also, various algorithms are generally known to determine the location of the image fiducial points. The image fiducial points can be produced in the image data by the fiducial markers 48, particular landmarks, or a contour (e.g. a 3D contour) of the patient 14 during acquisition of the image data.

Once the physical fiducial points and the image fiducial points have been identified, the image space and the physical space can be registered. A processor, such as a processor within the workstation 28, can determine registration of the patient space to the image space. The registration can be performed according to generally known mapping or translation techniques. The registration can allow a navigated procedure using the image data.

Figure 2:
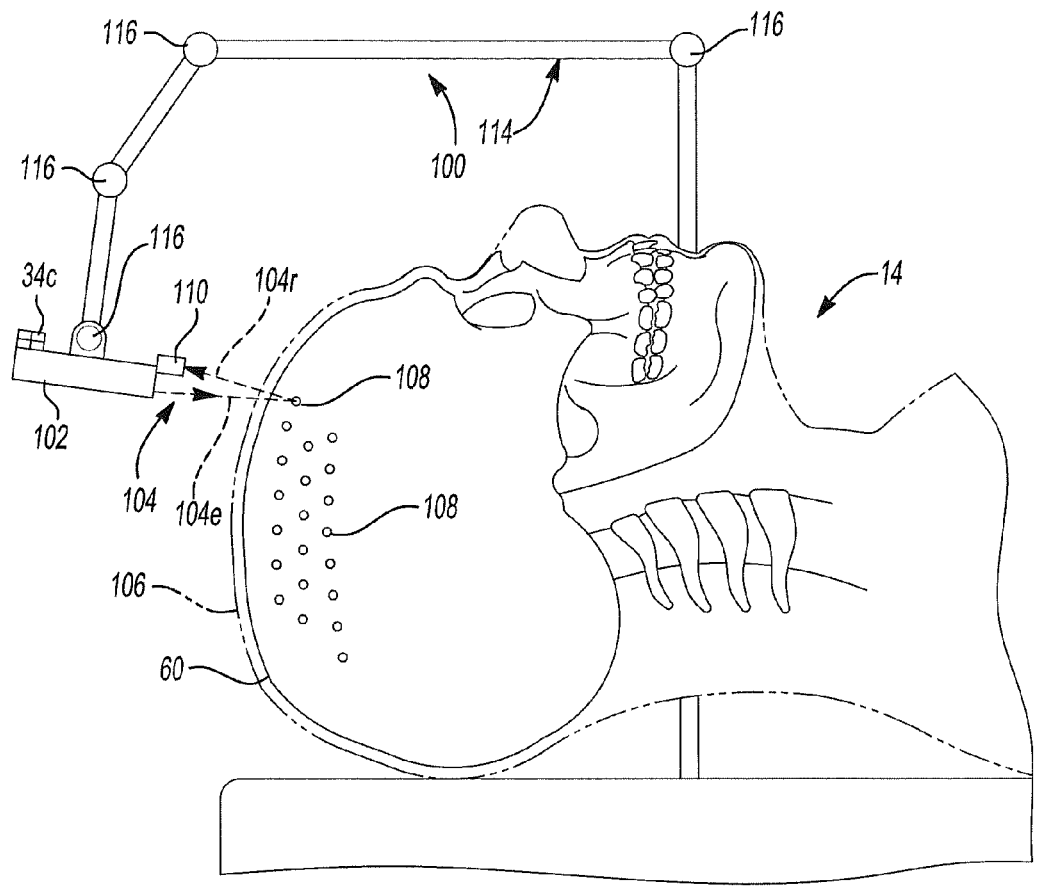
FIG. 2 is a detailed environmental view of a skin penetrating laser system.

According to various embodiments, a fiducial marker-less system can use a soft tissue penetrating or bone position determining laser system 100, as illustrated in FIG. 2. The skin penetrating laser system 100 can include a laser generator 102 that can direct a laser beam 104 to reflect off a bone structure, such as the cranium or skull 60 by penetrating through soft tissue 106, including dermis, circulatory tissues, muscle, vasculature, and the like. Although the current discussion relates to a procedure near the cranium 60, a procedure can also occur near other anatomical portions of the patient 14. Thus, the laser beam 104 may be required to pass through more or less soft tissue than near the cranium 60. For example, a great amount or mass of muscle tissue may be present near a spinal column, femur, etc. One skilled in the art will understand that the amount and type of soft tissue to penetrate can also require the laser beam 104 to be of an appropriate power, wavelength, etc. that can differ depending upon the amount and type of soft tissue to penetrate.

The laser beam 104 can include an emission beam 104e and a reflection beam 104r. The emission beam 104e can impact or contact the bone structure, including the cranium 60, at a point or virtual physical fiducial point 108. The reflection beam 104r can then reflect, according to generally understood physical requirements, to a receiver, such as a receiver 110 associated with the laser device 102. The reflection occurs at a point or reflection point which can be the virtual physical fiducial point 108. The reflection point can be interpreted or determined to be the virtual physical fiducial point 108 for purposes of correlation or registration, as discussed further here.

A receiver 110 can receive the reflected beam 104r from the virtual physical fiducial point 108 and determine a distance of the virtual physical fiducial point 108 from the laser device 102. Determining a distance from the receiver to the virtual physical fiducial point 108 can be determined using various techniques. For example, a pulsed beam may be used and a time of transmission can be determined or a variance in phase can be used to determine distance traveled. Determining a distance with a laser beam, however, is generally understood by those skilled in the relevant art.

A position of the laser device 102 or the receiver 110 can be determined, according to various embodiments. For example, the position of the laser device 102 or the receiver 110 can be tracked with the tracking device 34a. The tracking device 34a can be tracked with the tracking system 46, as discussed above. This allows the navigation system 10 to determine the position of the virtual physical fiducial point 108 in the patient space.

The virtual physical fiducial point 108 can be manually or automatically correlated to a point in the image data 38. According to various embodiments, however, the laser device 102 can be moved to a plurality of positions relative to the patient 14 and the cranium 60. By moving the laser device 102 relative to the patient 14, a plurality of the virtual points 108 can be determined in the patient space. The laser device 102 can also be moved over relative to the patient 14 and a plurality of the physical fiducial points 108 can be determined while the laser device 102 is moved. Thus, one will understand, that the laser device 102 need not be moved to discrete points, but can be moved in a pattern relative to the patient 14 and the points can be collected while it is moved.

Once a selected number of virtual points 108 are created or determined the processor, such as in the workstation 28, can match a contour determined via the physical fiducial points 108 and a contour determined in the image data 54. As discussed above, various techniques are known to determine contours based on the determined physical fiducial points 108 or in the image data. Examples include, edge detection, region growing, etc. Also, the contours, as discussed throughout, can include 2D or 3D contours, depending upon the amount of points or location of points and the type of image data. Systems that can be used to obtain contour information or provide enough points to determine a contour in physical space, as discussed above, can also be referred to contour determining systems.

The contour of the patient 14 can be determined by determining the plurality of the fiducial points 108 on the patient 14 with the laser device 102. Various algorithms can also be used to determine a contour of the patient 14 with a plurality of the virtual physical fiducial points 108, prior to determining a match to contours in the image data. For example, the physical fiducial points 108 can be related to one another define a line or 3D contour of the patient 14 that can be correlated to a contour determined in the image data 38. One skilled in the art will understand that the various distinct points can also be used to perform the registration, thus the 3D contour as the fiducial points is merely exemplary.

The laser device 102 can be interconnected to a stand or manipulation arm 114 that can include one or more moveable joints 116. The moveable joints 116 can be robotically manipulated or controlled, such as with the workstation 28. Alternatively, the moveable joints 116 can be moved by a user, such as the user 42. A tracking device 34c can be used to determine the position of the laser device 102 in the physical space to compare or register the image data to the physical space. The position of the laser device 102 can also be determined via a position algorithm, if the stand mechanism 114 is robotically controlled or includes various movement or position determination devices, such as potentiometers, stepper motors, or the like.

The laser device 102, which can have the tracking device 34c associated therewith, can be the device 12. As illustrated in FIG. 1, the device 12 can be independently held by the user 42 and can be moved relative to the patient 14. Thus, the laser device 102 can also be held by the user 42, free of the stand 114, and moved relative to the patient 14 to determine a line, 3D contour, or any selected number of distinct physical fiducial points 108.

The laser device 102 can be any appropriate laser device. The laser device 102 can produce the beam 104 that is operable to substantially pass through soft tissue surrounding a substantially rigid structure, such as a bone structure including a cranium 60, and reflect off the rigid structure. The laser device 102 can emit any appropriate laser beam, such as one that includes a wave length of about 750 nanometers to about 810 nanometers.

The rigid structure of the bone, including the cranium 60, can be effectively used to register image space to the physical space. The structure of the bone rarely changes shape or configuration between the time of the acquisition of the image data and the determination of the virtual points 108, either during or immediately preceding a surgical procedure. The bone structure, therefore, can provide an appropriate structure for comparison between the physical space and the image space.

The physical fiducial points 108 can be located on the patient 14 according to various embodiments. For example, the patient 14, including the cranium 60, can be fixed in the physical space. Thus, the physical fiducial points 108 are fixed in physical space once they are determined. Also, a DRF, such as the DRF 44, can be interconnected with the patient 14. When the DRF 44 is attached, the patient 14 can move and the physical fiducial points 108 can still be related to one another within the physical space and the navigation system 10 because of the DRF 44 tracking the movement of the patient 14.

A receiver or sensor 110 can receive the reflected beam 104*r* to determine the position of the point 108. The processor, such as the processor on the workstation 28, can determine the distance between the laser device 102 or the tracking device 34*c* to determine the position of the virtual fiducial point 108. The determination of a distance based upon a reflected laser beam is well understood in the art.

As discussed above, matching or correlating of a contour in the physical space and a contour in the image space can be used to register the image space and the physical space. The physical space, including the patient space, can have a contour defined by one or more of the fiducial points 108. The contour can also be referred to as a fiducial point alone. This can allow the laser system 100 to act or perform a contour determination or act as a contour forming system. A contour can also be defined in the image data in the image space, using generally known techniques and algorithms that can be performed by the processor. Further, the contours from the image space can then be matched to the contours in the physical space to perform a registration of the image space to the physical space.

The registered image space to the physical space can then be used in a surgical navigation procedure, such as the placement of a micro-electrode or deep brain stimulation electrode in the cranium 60. As discussed above the various physical fiducial points 108 can be determined and, if desired, a contour can be determined from a plurality of the physical fiducial points 108. The contour or the plurality of the physical fiducial points can be used to match or correlate to the image space. The image data can then be used to navigate the selected procedure.

A registration can be performed without the fiducial markers 58 using the laser system 100. The laser system 100, however, is a contour determination system or fiducial marker-less registration system, according to various embodiments. Contour determination systems or fiducial marker-less registration systems can also include various tracked portions, as discussed herein.

Figure 3:
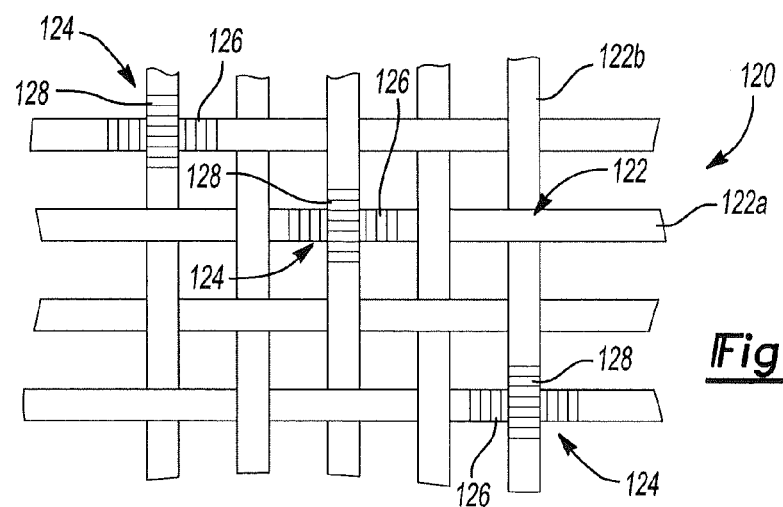
FIG. 3 is a detailed view of a flexible member including tracking devices, according to various embodiments.

According to various embodiments, with reference to FIG. 3, a flexible sheet or member 120 can include one or more fibers 122. The fibers 122 can include woven fibers, for illustration purposes only, that include longitudinal fibers 122*a* and latitudinal fibers 122*b*. Nevertheless, the fibers can be woven into any appropriate material, such as a sheet, a drape, and the like. Moreover, the member 120 can be sized with any appropriate dimensions, such as to cover a selected portion of the anatomy.

The fibers 122 of the member 120 can have a tracking device 124 formed around them or relative to them. According to various embodiments, the tracking device 124 can include a first coil member 126 and a second coil member 128. The two coil members 126, 128 can be substantially perpendicular to one another and be used with the tracking system 46 and can be similar to the tracking devices 34. The sheet 120 can include a plurality of the tracking devices 124 that can be positioned at selected points, such as about one millimeter apart, two millimeters apart, one centimeter apart, or any appropriate dimension. As discussed above, the tracking devices 124 can, according to various embodiments, sense a strength of a field, such as an electromagnetic field, produced by the localizer device 48. Therefore, the sheet 120 including the plurality of the tracking devices 124 can provide a plurality of tracked positions relative to whatever the sheet 120 is placed over. As discussed above, the tracking devices can be tracked relative to the patient 14.

It will be understood that the tracking devices 124 that can be associated with the sheet 120 can be any appropriate type of tracking device. For example, optical tracking devices, including active optical or passive optical members, can be used as tracking devices with the tracking system 46'. The active optical members, including light emitting diodes (LEDs) can be associated with the sheet 120. Similarly, passive optical members, including reflectors, can be associated with the sheet 120. The tracking devices 124 can either emit or reflect optical wavelengths to the optical tracking system 46' and the position of the optical tracking devices can be tracked, as is generally understood in the art. Thus, one skilled in the art will understand, any appropriate tracking system can be used and any appropriate tracking device can be associated with the sheet.

The sheet 120, as mentioned briefly above, can be dimensioned to be positioned on the patient 14. For example the sheet 120 can cover an expanse and be placed to cover an exterior portion of the patient 14. The sheet 120 can also be provided to maintain a sterile field relative to the patient 14. The sheet 120 can, generally, include a top and bottom surface covering an expanse and a relatively thin edge. The sheet 120 can be substantially flexible to drape over and conform to a selected portion of the patient 14.

As discussed herein, the plurality of tracked points can provide information relating to the position of each of the tracking devices 124 on the patient 14. The information can be used for tracking the patient 14, determining the contour of the patient 14, registering image space to patient space, or the like.

Figure 5:
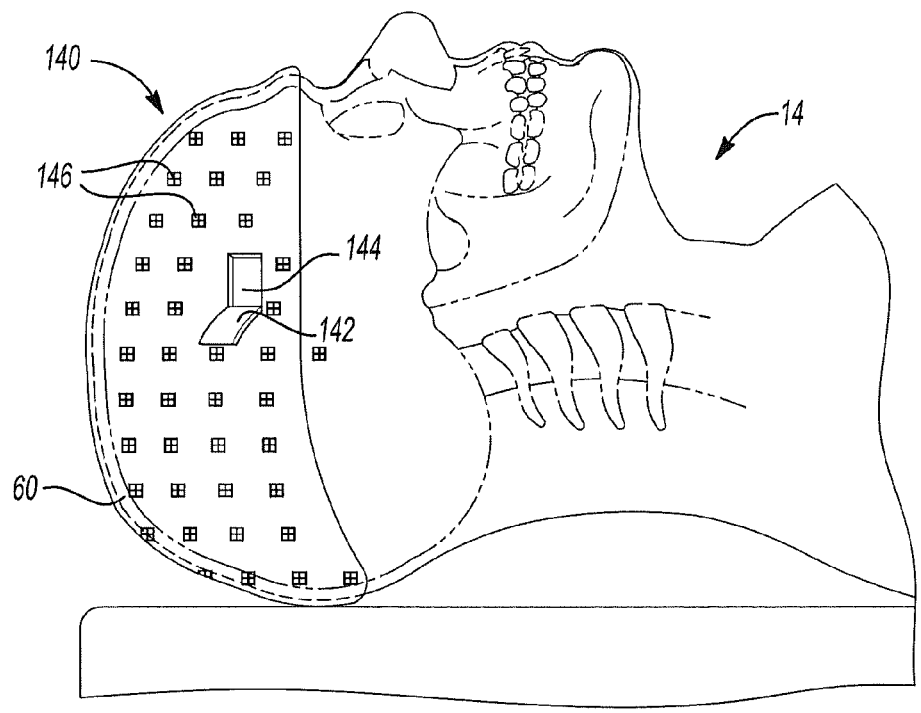
FIG. 5 is a detailed environmental view of a flexible member including a plurality of tracking devices.

The sheet 120 can be sized or dimensioned to cover any appropriate portion of the patient 14. For example, a large single sheet can be formed to cover a portion of the cranium 60 (FIG. 5). Also, a long narrow sheet can be formed to wrap around a selected anatomical portion. In any case, the plurality of the tracking devices 124 or selected tracking device can be used to provide position information at a plurality of points on the patient 14.

The plurality of the points can be physical fiducial points. The physical fiducial points can be similar to the physical fiducial points 108 and can be used alone or to define a physical space 3D contour. The physical space contour or fiducial point can be correlated to a 3D contour or image data fiducial point. Thus, providing the plurality of the tracking devices in the sheet to provide position information at a plurality of points can provide information similar to the physical fiducial points 108.

According to various embodiments, a 3D contour can be determined based upon the tracking devices associated with the sheet 120. The contour can be compared to and matched to a contour in the image data. Alternatively, or in addition thereto, the sheet 120 and the tracking devices can be used as fiducial points and can be imaged with the patient 14. Thus, the tracking devices, or portions associated therewith, can be imaged and produce image fiducial points to be correlated to physical space fiducial points.

Figure 4:
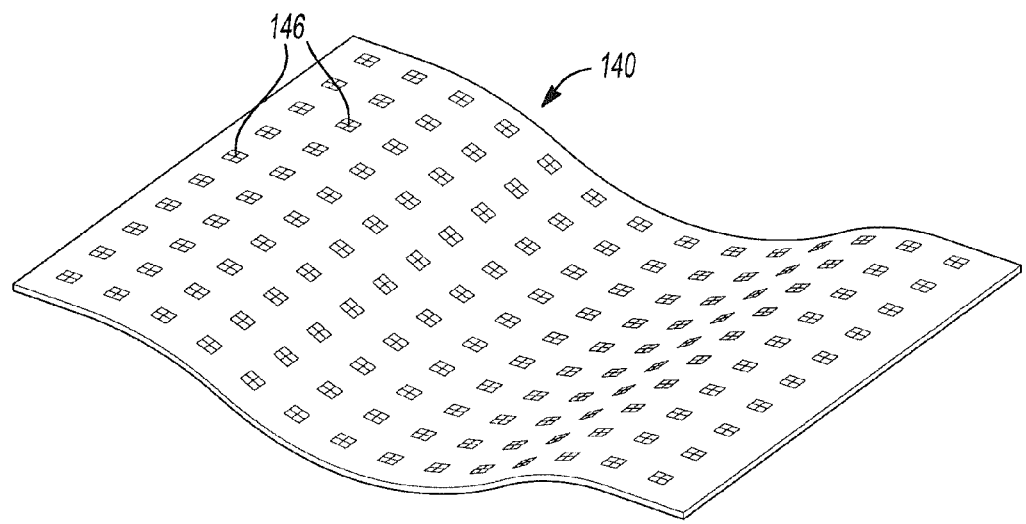
FIG. 4 is a detailed view of a flexible member including tracking devices, according to various embodiments.

According to various embodiments, a flexible member or sheet 140, with reference to FIG. 4, can be provided of a substantially continuous material. For example, the sheet 140 can be formed of a polymer or other substantially non-porous material. The sheet 140 can include the Steri-Drape® surgical drapes sold by 3M Company Corporation of St. Paul, Minn. The surgical drapes allow for maintaining a sterile field around a selected portion of the patient 14. The sheet 140, as mentioned briefly above, can be dimensioned to be positioned on the patient 14. For example the sheet 140 can cover an expanse and be placed to cover an exterior portion of the patient 14. The sheet 140 can also be provided to maintain a sterile field relative to the patient 14. The sheet 140 can, generally, include a top and bottom surface covering an expanse and a relatively thin edge. The sheet 140 can be substantially flexible to drape over and conform to a selected portion of the patient 14.

The sheet 140 can be pierced or cut for access to a particular location, such as a position on the cranium 60 of the patient 14. The sheet 140 can also include a flap 142 that can be moved or removed to gain access through a portal 144 to a selected region of the cranium 60.

The sheet 140 can include a tracking device 146 or a plurality of the tracking devices 146. The tracking devices 146 can be positioned in the sheet 140 in any appropriate manner. For example, the tracking devices 146 can be positioned within the sheet 140 in a substantially grid or aligned manner. The tracking devices 146 can be positioned with regular spacing from one another to provide for a plurality of trackable points or positions, similar to the coil pairs 124, 126 of the sheet 120.

The tracking devices 146 can also include optical tracking devices, as discussed above. The optical tracking devices can be active or passive tracking devices. The optical tracking devices can work with the optical tracking system 46' to provide position information of the patient 14. Also, the sheet 140 can be placed on the patient 14 while image data is being acquired of the patient 14. Thus, the sheet 140 can also be used to produce image fiducial points, as discussed above.

With reference to FIGS. 3 and 4 and additional reference to FIG. 5, the exemplary sheet 140 can be draped over the patient 14, such as over the cranium 60. The sheets 120, 140, according to various embodiments can include a selected flexibility or stiffness. The sheets 120, 140, can be flexible enough to substantially conform to a surface contour of the patient 14. Also, the sheets 120, 140 can be light enough to be placed on the patient 14 without substantially deforming the soft tissue around the boney structure. Thus, the determined contour of the patient 14 with the sheets 120, 140 can be substantially similar to a contour of a surface of the patient 14 with no covering.

Also, as discussed above, the sheets 120, 140 can be used to maintain a sterility relative to the patient 14. The sheets 120, 140 can cover or define an expanse. The sheets 120, 140 can be provided to be draped over or conform to a selected portion, such as an exterior surface, of the patient 14

The tracking devices 146 associate with the sheet 140 can be flexible or of an appropriate dimension to be positioned over the cranium 60 in a substantially close manner. As discussed above, the sheet 140 can be substantially similar to surgical sterile sheets so that the sheet 140 can substantially match the outer contour of the dermis or skin of the patient 14 by being substantially in contact with the surface of the patient 14.

The sheet, such as the sheet 140 can also include various modular or openable portions 144. The open or flap portion 144 can allow for access to various portions of the anatomy of the patient 14 without removal or separately cutting through the sheet 140. The tracking devices 146 can be positioned near or around the flap portion 144 to allow for substantially precise determination location of an area around the flap portion 144. Further, the sheet 140 can be positioned to cover a selected portion of the anatomy or cling to a selected portion of the anatomy to precisely define or substantially precisely position the coils 124,126 or the tracking devices 146 at selected locations relative to the patient 14.

The sheets 140, 120 can also include a selected weight or mass that does not does substantially compress or deform the soft tissue of the patient 14. For example, a fiducial marker or trackable device can be interconnected with the patient 14 that deforms soft tissue surrounding bone of the patient 14. The deformation of the soft tissue with the tracking device or while positioning the tracking device can introduce certain inaccuracies into the navigation or tracking system 46. Thus, the sheets 120, 140 can be provided with an appropriate mass, density, mass evenness, and the like to substantially remove or eliminate the possibility of an unwanted or undesired deformation. Although a deformation can be accounted for in a tracking system or a navigation system 10, removing the possibility of such deformation can assist in the efficiency of the navigation system 10.

The sheets 120. 140 can also be formed to include a selected shape or 3D contour. For example, the sheets 120, 140 can be formed to include a shape that substantially matches a portion of the patient's 14 anatomy, including the cranium 60. Thus, the sheets 120, 140 can be efficiently positioned in a selected location. Also, the sheets 120, 140 can be preformed and flexible for a substantially custom or unique fit to the patient 14.

Further, the tracking devices 146 positioned within the sheet 140 can also then substantially contact the skin or be positioned relative to the skin to provide position information in concert with the tracking system 46. As discussed above, the tracking devices 146 can be tracked with the tracking system 46 to determine the position relative to the patient 14. The coils 124, 126 in the sheet 120 can be formed to contact the skin or surface of the patient 14 as well.

The tracking devices 146 can include any appropriate dimension, which can be substantially identical to a thickness of the sheet 140. Therefore, the tracking devices 146 can substantially contact the skin of the patient 14, relative to which the sheet 140 is positioned. In addition, the tracking devices 146 can include a selected dimension to position within the sheet 140 at a selected depth or orientation. Also, the coil pairs 124, 126 in the sheet 120 can substantially contact the surface on which the sheet 120 is positioned by the configuration of coils 124, 126 on the fibers 122. According to various embodiments, the coils 124, 126 or the tracking devices 146 can be configured in the respective sheets 120, 140 to contact the skin of the patient 14 for selected accuracy.

The tracking devices 146 and the coil pairs 124, 126 can be wired, wireless, or any appropriate configuration to transfer information to the tracking system 46 to allow a determination of the location or position of the tracking devices 140 and coils 124, 126. The positioning of the plurality of tracking devices 140 relative to the patient 14 can allow for a plurality of data point or patient points to be tracked by the tracking system 46. The plurality of points can effectively define a contour or surface of the patient 14. The contour can be a 2D or 3D contour of the patient 14.

As discussed above, certain contour matching algorithms can be used to register patient space to image space. By tracking the plurality of the positions of the tracking devices 146 or the coils 124, 126 can provide the contour information that can be matched or registered to contours represented in the image data. Therefore, the sheets 120, 140 can be provided to allow for registration of the patient space to the image space. The sheets 140, 120 can also be provided for various purposes such as covering the patient, providing a sterile field in an operating room, or other purposes.

Thus, the sheets 120, 140 can be placed on the patient 14 and the tracking devices in the sheets can be tracked to determine one or more physical fiducial points. A plurality of the determined fiducial points can be used to define a contour of the patient 14. The contour of the patient 14 can then be matched to a contour that is determined in the image data, as discussed above. The matching of the contours can be used to register the image space to the physical space. The registered image data can be used in a navigated procedure.

As discussed above, the navigation system 10 can be used to navigate various instruments relative to the patient 14, such as a catheter, a lead (e.g. a DBS, or micro-electrode lead), or the like into the cranium 60. The various devices, including the laser system 100, the sheets 120, 140 and the like, can be used to provide information within the navigation system 10 to allow a determination of a registration between the image space and the patient space. Various other systems can also be used to perform a registration of image space to physical space without fiducial markers 58. For example, the Tracer™ sold by Medtronic Inc. can include an instrument that can be positioned at several points or drawn across a skin surface and tracked within the tracking system 46 to determine a contour of a skin surface. Similarly, the Fazer® Contour Laser System sold by Medtronic, Inc. can be used to determine or scan across a skin surface to determine a skin surface for registration. The determined skin surface can then be matched or used to register the image space to the patient space.

According to various embodiments, a contour determining device or system (e.g. the laser system 100, sheets 120, 140, the Fazer™ Contour Laser System, etc.) can be used to locate or determine various points on the patient 14. The points can be fiducial points that include a single point or a contour (i.e. 2D or 3D). Moreover, the various contour determining devices can be tracked with the tracking systems 46, 46'. The position of the contour determining devise can be processor or determined in a processor in the tracking system alone or in the works station alone 28, or combinations thereof. Also, the information collected with the tracking system 46, 46' can be transferred to any appropriate processor for position determination. According to various embodiments, a separate processor or the same processor can also perform the registration of the image space to patient space and determine the position of the tracked instrument relative to the image data.

Figure 6:
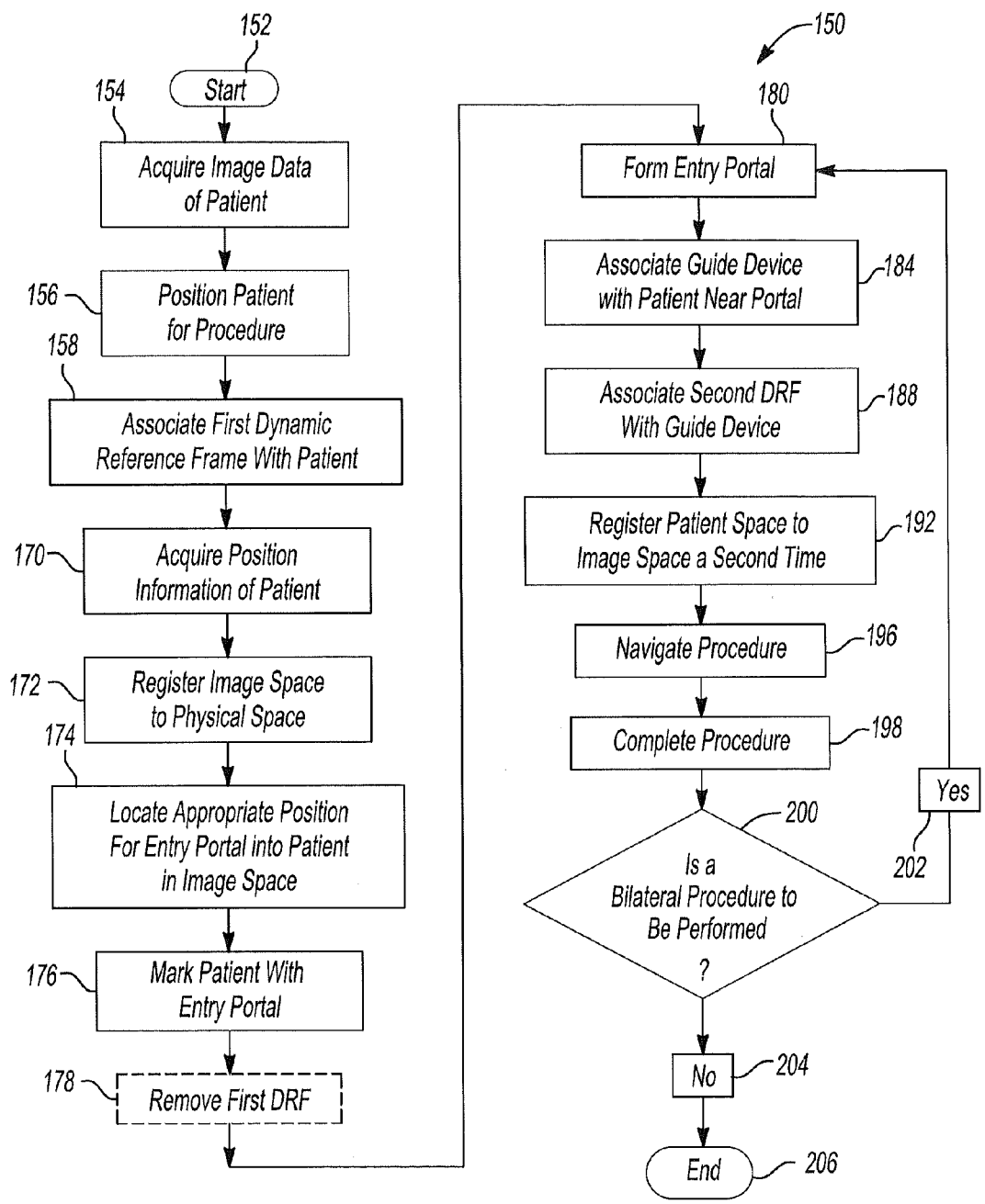
FIG. 6 is a flow chart of a process for performing a selected procedure.
Figure 7:
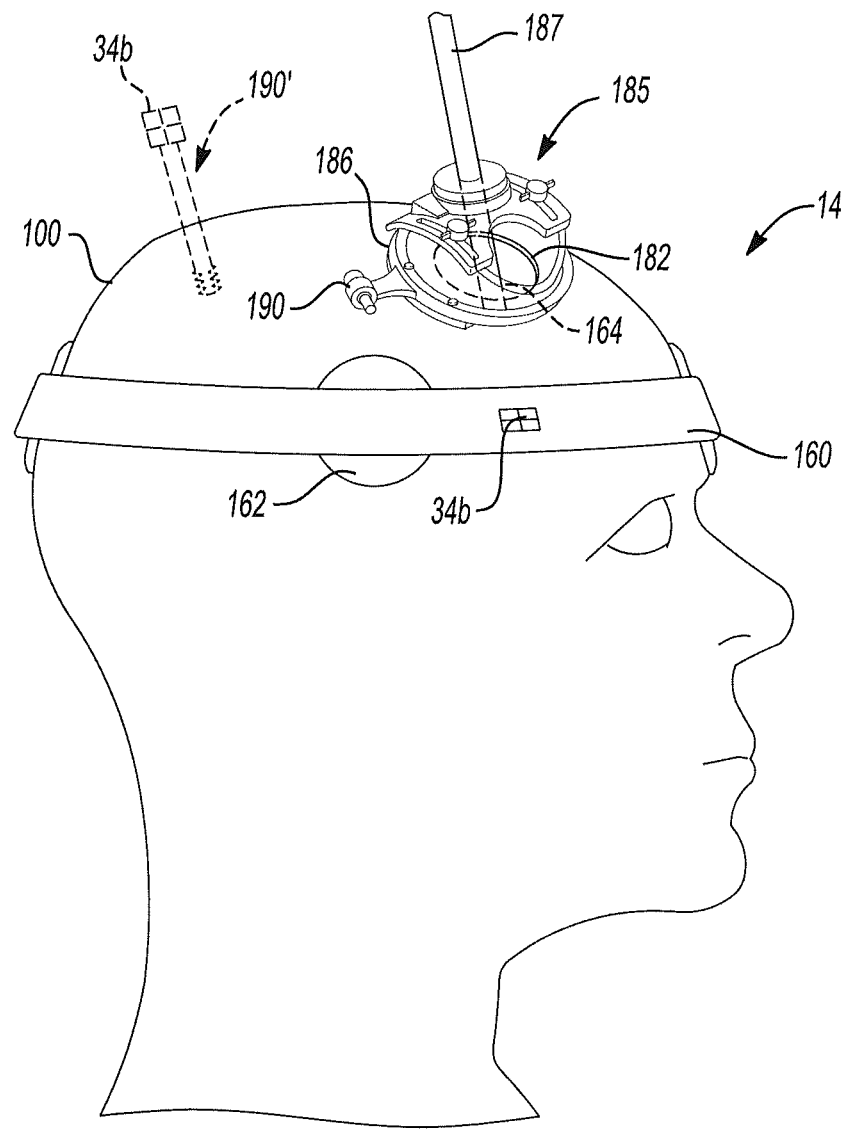
FIG. 7 is an environmental view of a patient including various elements associated therewith.

According to various embodiments, with reference to FIG. 6, a navigation system, such as a navigation system 10, can be used to perform a procedure according to various processes. A method of performing a registration and surgical procedure 150 is illustrated, which can use the navigation system 10. In the procedure 150, various and multiple registrations can occur via fiducial or fiducial marker-less systems, including those discussed above. The method 150 is described in relation to a selected procedure, such as a cranial or deep brain stimulation procedure, but can be used for any appropriate procedure on the anatomy. Therefore, the discussion herein relating to a cranial or deep brain stimulation procedure is merely exemplary.

Briefly, the method 150 can be used to perform a first registration of the image space to the physical space, perform a first procedure, perform a second registration, and perform a second procedure. The two separate registrations can be used to account for the differing accuracies that can be used in performing the two separate procedures. For example, a first procedure can be performed with a first registration accuracy and a second procedure can be performed with a second greater registration accuracy.

The method 150 starts at start block 152. At block 154 image data acquisition of the patient is performed block 154. The image data acquired of the patient can be any appropriate image data such as image data acquired with the imaging device 34. Although, any appropriate imaging device can be used such as a magnetic resonance imaging device, a computed tomography imaging device, an ultrasound imaging device, or any appropriate imaging device. The acquired image data can be acquired preceding a procedure or during a procedure. In addition, the image data acquired in block 154 can be acquired at any appropriate time. Further, the patient 14 can have fiducial points associated with the patient, such as the fiducial markers 58 or any other appropriate fiducial markers. Moreover, the image data acquired in block 154 can be registered to the patient space according to various techniques, including those discussed above, without the use of fiducial markers.

As discussed above, the patient 14 can have fiducial markers, such as the fiducial markers 58 associated therewith. The fiducial makers 90 can be any appropriate fiducial marker such as fiducial markers that can act both as image-able fiducial markers to create fiducial points in image data and fiducial markers that can be touched or found in physical space. For example, fiducial markers can include the markers sold by IZI Medical Products of Baltimore, Md. The fiducial markers can include a portion that can be imaged with a selected imaging process and can also be found in physical space. Finding the image data portion defining the fiducial marker and correlating it to the fiducial marker in physical space can allow for registration.

It will also be understood that including a fiducial marker with the patient 14 during imaging may not be required. For example, the Tracer® registration system, Fazer® Contour Laser, the skin penetrating laser 102, the sheets 120, 140, or the like can be associated or used to determine the contour of the patient 14 after the image data is acquired. As discussed above, various contour matching algorithms can be used to match or register the physical space of the patient 14 to the image data. Therefore, although fiducial markers can be associated with the patient 14, fiducial markers are not required for registration of a physical space to the image space and a fiducial marker-less registration can also be performed.

After the image data is acquired, or concurrently or prior thereto, the patient can be positioned for the procedure in block 156. A first dynamic reference frame including a tracking device 34d can be associated with the patient 14 in a substantially non-permanent or non-invasive manner. The dynamic reference frame including a tracking device 34d can be associated with and attached to the patient with a first holder 160. The first holder 160 can be an easily removable and non-invasive, such as the Fess Frame™ holding device sold by Medtronic, Inc. Generally the first holder 160 can be efficiently removed, at least in part due to the surface contact members or holding members 162, such as suction cups or anti-slip feet. The surface contact member 162 generally contacts a surface of the patient 14, such as an outer surface of the skin of the patient 14. The first holder 160 can be associated with the patient 14 in any appropriate manner, such as after positioning the patient 14 for a procedure and positioning the first holder 160 on the patient's cranium 60.

The course registration can include a selected accuracy, such as about +/−0.5 to about +/−3 millimeters, including about +/−1 to about +/−2 millimeters in navigational accuracy. The accuracy achieved of the registration with the first holding device 160 can be appropriate for identifying a planned position for a burrhole 164. As discussed herein, the planned position of the burr hole 164 can be identified relative to the patient 14 within a selected accuracy that can be less than the required accuracy for navigating a lead or device into the patient 14.

After the dynamic reference frame is associated with the patient in block 158, position information can be acquired of the patient in block 170. The position information acquired of the patient in block 170 can include the identification of locations of fiducial markers, such as the fiducial markers 58 on the patient 14. As discussed above, the identification of the location of the fiducial markers 58 on the patient 14 can be performed by tracking the device 12 and touching or associating it with one or more of the fiducial markers 58. The navigation system 10 can then register the patient space to the image space, as discussed above.

In addition, various fiducial marker-less registration techniques can be used, including those discussed above. For example, the Tracer® registration system and Fazer® Contour Laser can be used to identify contours of the patient 14 to allow for a contour matching and registration to the image space. In addition, the skin penetrating laser system 100 can be used to identify various virtual fiducial points 108 on the patient 14 to assist in the identification of various points and identify contours of the patient 14, again for registration. Further, the various drapes or sheets 120, 140 can include a plurality of the tracking devices or coils to provide information relating to positions or contours of the patient 14. Therefore, the patient space can be registered to the image space according to any appropriate technique including identifying contours of the patient 14 for registration to image data acquired of the patient in block 154.

Once position information of the patient is acquired in block 170, a first or course registration can occur in block 172. As discussed above, the registration using the acquired position information in block 170 and the first dynamic reference frame associated with the patient in block 158 can include a selected registration accuracy. The registration accuracy can be any appropriate accuracy such as about 1 millimeter or greater. The accuracy achieved with the first dynamic reference frame attached in block 158 can be used for various portions of the procedure, such as identifying the planned entry portal or burrhole location 164 on the patient 14. As is understood by one skilled in the art, the planned location of the entry portal 164 can be identified on the image data acquired in block 154. Once the image space is registered to the physical space, the planned position of the entry portal 164 can be transferred to the patient 14. This allows the determination of an appropriate position for the entry portal into the patient in block 174. The planned position for the entry portal can be marked on the patient in block 176. Due to the registration accuracy with the first dynamic reference frame position of the entry portal will include a similar accuracy.

The entry portal can include a selected accuracy or lack of accuracy for various reasons. For example, a navigation frame, such as the NEXFRAME® stereotactic system sold by Medtronic, Inc. can include a selected amount of navigational positioning or movement. Therefore, according to various embodiments, if the marking of the entry portal on the patient 14 is within a selected accuracy, the guiding device can be positioned to achieve an appropriate trajectory of an instrument into the patient 14. It will be understood that the guiding device need not be used in navigating an instrument.

After the planned position of the entry portal, as marked in block 176, the first dynamic reference frame may be optionally removed in block 178. It will be understood that the first dynamic reference frame can remain on the patient 14 during a complete procedure and removal of the first DRF is merely optional. Removal of the first DRF, however, can allow for easy or efficient access to various portions of the patient 14 by the user 60.

The entry portal can then be formed in the patient 14 in block 180. The entry portal 182 can be formed near or at the planned position 164. The entry portal 182 can be formed using any appropriate instruments, such as a generally known burrhole forming device to form at the entry portal 182 into the patient 14. After the entry portal is formed in the patient a guiding or alignment device 185 including a base 186 can be associated with the patient near the entry portal in block 184. The guiding device 185 can be any appropriate guiding device, including the NexFrame™ frame sold by Medtronic, Inc. Nevertheless, any appropriate guiding device can be used, such as a stereotactic head frame, including the Leksell® Stereotactic System head frame sold by the Elekta AB of Sweden. An instrument 187 can be guided with the guiding device 185. Alternatively, a guiding device need not be used and an instrument or appropriate device can be independently navigated into the patient 14 without a guide device.

A second dynamic reference frame 190 can be associated with the patient 14 or the guiding device 185 in block 188. The second dynamic reference frame 190 can be formed with the guiding device 186, affixed to the guiding device 186, or positioned in an appropriate manner. The second dynamic reference frame 190 can be integrally formed with the guiding device 186 or interconnected with the guiding device 186. For example, an EM tracking device can be associated or formed with a starburst connector to be connected to the guiding device. Starburst type connectors can include those disclosed in U.S. patent application Ser. No. 10/271,353, filed Oct. 15, 2002, now U.S. Pat. App. Pub. No. 2003/0114752, incorporated herein by reference.

The second dynamic reference frame 190 can be substantially rigidly affixed to the patient 14 either directly or via the guiding device 186. As is understood, if the dynamic reference frame 190 is associated with the guiding device 186, the number of invasive passages or incisions into the patient 14 can be minimized. It will also be understood, that the second DRF can be attached as an alternative second DRF 190' that can be attached directly to the cranium 60 of the patient 14 rather than, or in addition to, to the guide device 186. A bone engaging member can be used to mount the tracking device 34d directly to the bone of the cranium. Regardless, the second DRF 190 is generally invasively fixed to the patient 14.

Once the second dynamic reference frame 190 is fixedly associated with the patient 14, a second or fine registration can occur in block 192. The second registration performed in block 192 can use the same or different registration fiducial markers or a fiducial marker-less system, similar to the acquisition of position information in block 170. Then the registration of patient space to the image space in block 192 can include the acquisition of position information of the patient and registering to the image space.

The rigid association of the second DRF 190 with the patient 14, however, can maximize the accuracy of the registration. According to various embodiments, the accuracy of the second registration can be higher than the accuracy of the first registration by any appropriate amount. For example, the fine registration can be 1 time to 100 times more accurate, including 1 time to about 10 times more accurate. For example, the accuracy of the registration via the second DRF 190 can be less than about +/−1 millimeter. For example, the accuracy can be about +/−0.1 millimeters to about +/−0.9 millimeters. The accuracy of the fine registration can allow for substantially precise navigation or positioning of instruments or devices relative to the patient 14. For example, navigation of the guide device 186 can be substantially precise to allow the navigation of a selected instrument or therapeutic device 194. The accuracy of the registration allows for the accuracy of the navigation and positioning of various portions relative to the patient 14.

Once the second registration occurs using or having the appropriate accuracy, the procedure can be navigated in block 196. The navigation of the procedure in block 196 can be any appropriate navigation such as navigation of a deep brain stimulation electrode, a micro-electrode electrode for recording, an implant, a navigation of a therapy delivering device (e.g. catheter), or any appropriate instrument or procedure. The procedure that can then be completed in block 198, such as implanting a deep brain stimulation electrode and fixing it with a Stimloc® lead anchoring device sold by Medtronic, Inc. or Image-Guided Neurologics, of Florida.

Once the procedure is completed in block 198, a decision block whether a bilateral procedure is to be performed can occur in block 200. If YES is determined in block 202 the formation of an entry portal in block 180 can be performed again at a second location, such as at a bilateral location of the patient 14. If a bilateral procedure is not occurring, the result block NO 204 can be followed and the procedure can be ended in block 206. Ending the procedure can include various appropriate functions such as completing an implantation, closing the incision of the patient 14, or other appropriate steps. For example, after the implantation of the deep brain stimulation electrode, the stimulating device can be programmed according to any appropriate technique.

Figure 8:
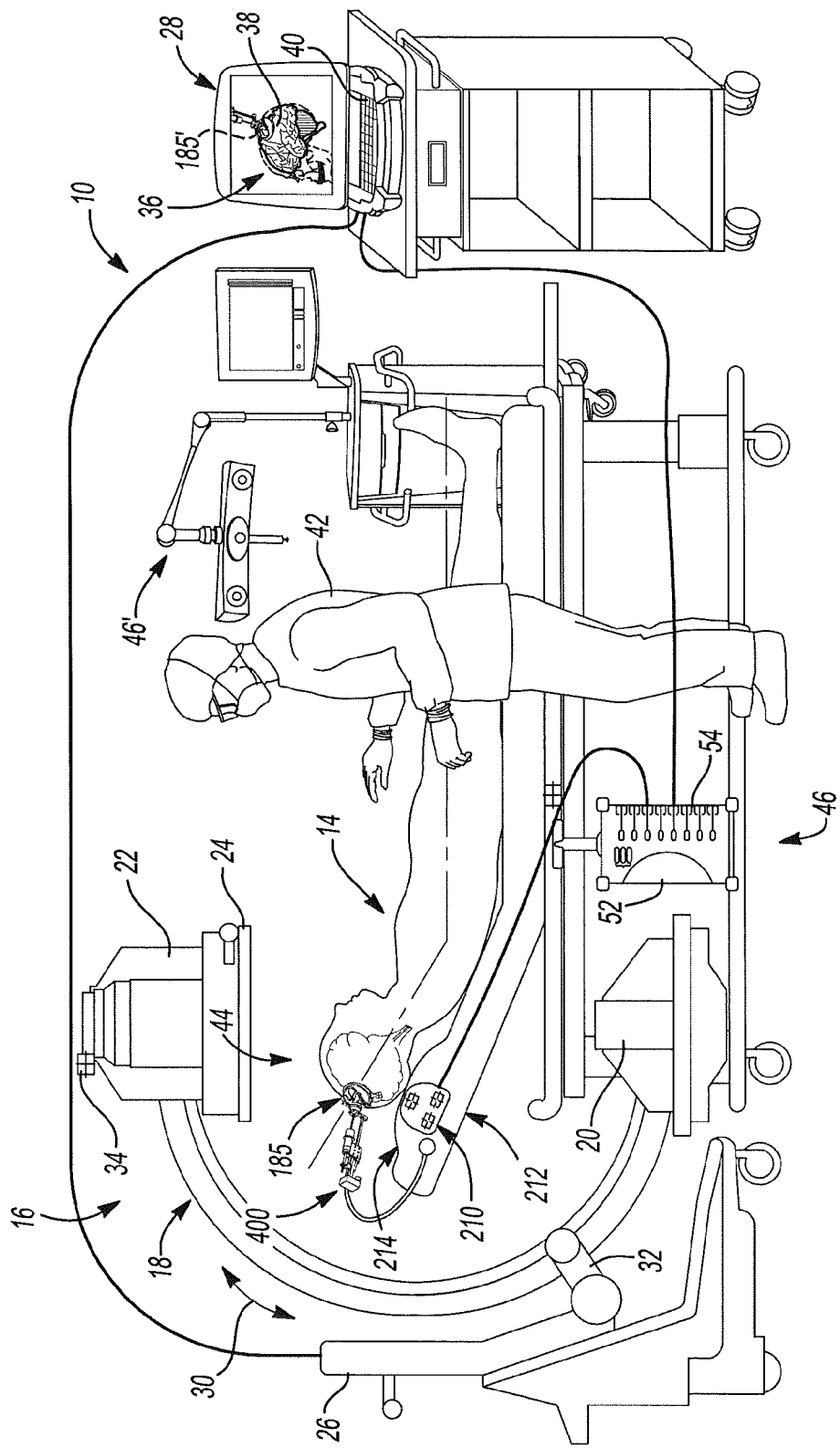
FIG. 8 is an environmental view of a navigation system, according to various embodiments.

With reference to FIG. 8, the procedure discussed above can be performed on the patient 14 using appropriate navigable instruments and devices. It will also be understood that the appropriate procedure can include electrical recording, deep brain stimulation probe placement, etc. A localizer 210 can be integrated or positioned into a portion of a patient support 212, such as a headrest, a bed, or the like. The localizer 210 can be positioned into the patient support 212 at any appropriate location. For example, the localizer 210 can be positioned in a headrest portion 214 of the patient support 212. The localizer 210 can then be used to generate a field relative to the patient, such as encompassing all or part of the patient's head. This placement can assist in providing or forming a navigation field in the patient space defined by the patient 14. For example, placing the localizer 210 into the headrest can form a field encompassing the cranium or skull 60 of the patient 14 with a small volume localizer, low power system, etc. Also, the localizer 210 can be integrated into the patient support 212 to reduce additional portions or pieces placed in operating room devices that need to be manipulated by the user 42. Therefore, the localizer 210 can be provided and the patient 14 can be positioned upon the patient support 212 at any appropriate time. Exemplary positioning elements that include localizer coils are also disclosed in U.S. patent application Ser. No. 10/405,068, filed Apr. 1, 2003, now published as U.S. Pat. App. Pub. No. 2004/0199072, published on Oct. 7, 2004, entitled "INTEGRATED ELECTROMAGNETIC NAVIGATION AND PATIENT POSITIONING DEVICE," incorporated herein by reference.

The localizer array 210 positioned within the patient support 212 can then be operated during a selected portion of a procedure. For example, the tracking system 46 can be used to operate the localizer array 210 to define a navigation field relative to the skull 60 of the patient 14 for various purposes, including those discussed herein. Integrating the localizer array 210 in the headrest removes a requirement of placing the localizer 210 near the skull 60 during the operative procedure, thereby eliminating a step of positioning a localizer. In addition, integrating the localizer array 210 into the headrest 214 can assist in minimizing movement of the localizer array 210 during a procedure.

The localizer array 210 can operate substantially similarly to the localizer array 48, 50 discussed above. An electromagnetic field can be generated to define a navigation area for navigating instruments and devices relative to the patient 14. Briefly, the localizer 210 can include one or more coils. Each of the coils can generate a navigation field, such as an electromagnetic field. In addition, each of the coils can include one or more coils, such as three mutually orthogonal coils. Thus, the localizer 210 can include nine total coils. Also, the localizer 210 can act as a receiver for fields generated by other coils. Thus, the localizer 210 can act as a generator or a receiver in the tracking system 42.

Figure 9:
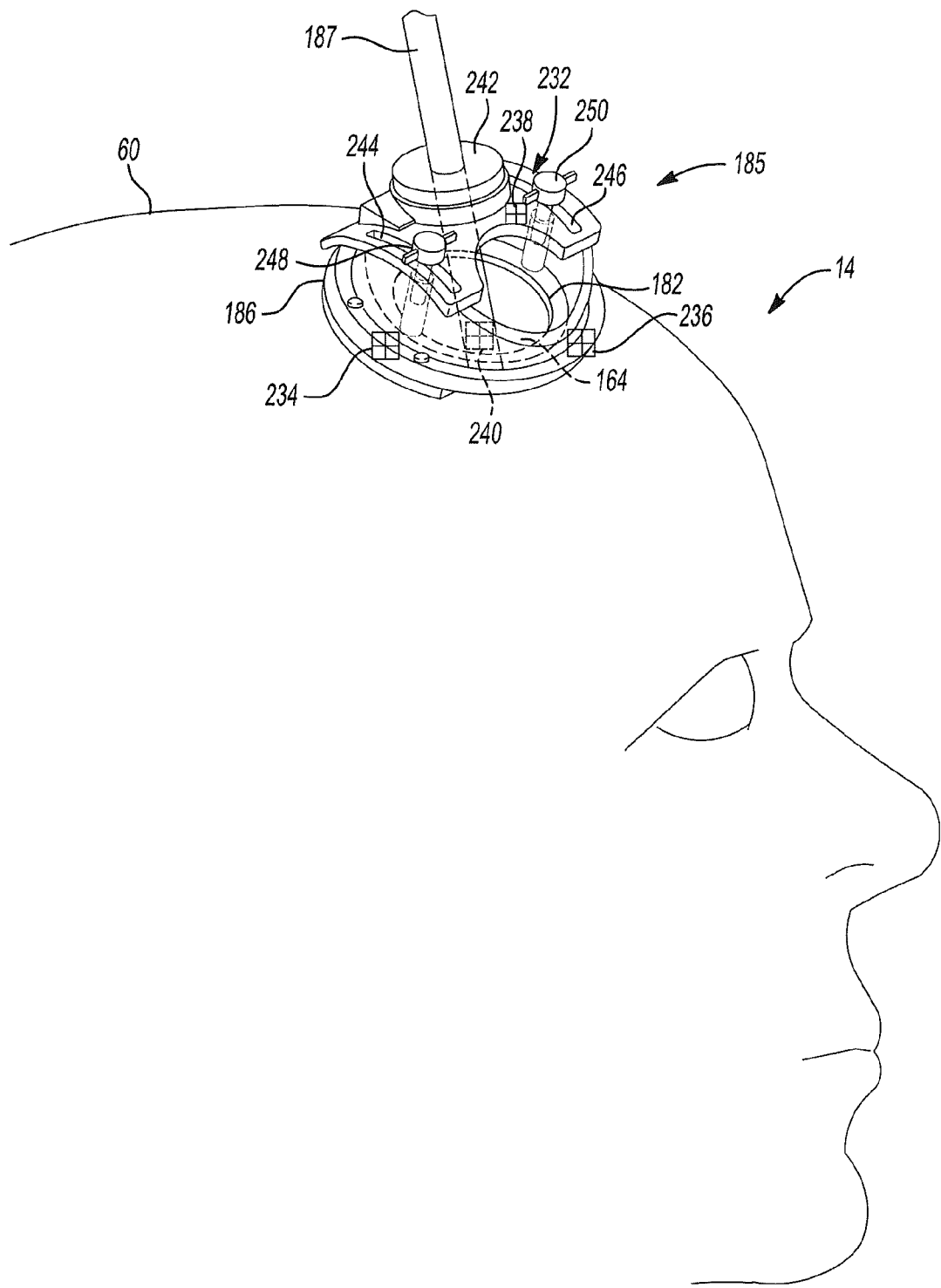
FIG. 9 is a detail environmental view of an alignment device 185 including an EM coil, according to various embodiments.

With additional reference to FIG. 9, the alignment system 185 can be positioned on the skull 60 of the patient 14. The alignment system 185 can include various portions, but generally includes the base 186 and a trajectory guide portion 232, the trajectory guide portion 232 is able to move relative to the base 186. The alignment device 185 can be substantially similar to that discussed above and be positioned relative to the burr hole 164.

In addition, the alignment device 185 can include various electromagnetic coils (herein, EM coils) for use with the tracking system 46. The alignment device 185 can include a first EM coil 234 that is fixed or positioned within the base 186. The base 186 can also optionally include a second EM coil 236. The trajectory portion 232 can further include a third EM coil 238. The EM coils 234, 236, 238 can be used for various purposes, as discussed further herein, including tracking the position of the base 186 and the trajectory guide 232. The EM coils can also be used as field generating coils for various reasons, such as guiding the instrument 187. Accordingly, the EM coils 234, 236, 238 can both generate a field and receive or sense a field generated by other coils, similar to the coils of the localizer 210. It will also be understood, that the coils of the system can be used in reverse of specifically described here. In other words, the first EM coil 234 can either sense a field generated by another localizer coil 210 or the first EM coil 234 can transmit a field to be sensed by the localizer coil 210. In either case, the position of the first EM coil 234 in the base 186 can be determined and this determination can be used for navigation of the base 186. Similar methods can be applied to navigating any other coils according to various embodiments.

In addition, reference to the coils 234, 236, 238 will be understood to include a single coil or more than one coil positioned relative to a second coil, such as orthogonally to one another. For example, each of the EM coils 234, 236, 238 can include three coils positioned orthogonally to one another.

The instrument 187 can also include a tracking sensor EM coil 240. The coil 240 on the instrument can be formed as one or more coils, as well. The instrument 187 can include one or members. For example, the instrument can include a guide tube in which another device, such as a deep brain stimulation probe or micro-electrode recorder, can be positioned. Thus, the instrument 187 can include a first portion that can be fixed in the trajectory portion 232 while another instrument portion moves within the tube. IN the alternative, the instrument 187 can be a single member. In the latter case, one or more EM coils can be positioned on both the tube and the instrument moveable within the tube. The multiple coils, on the instrument, base 186, or of the localizer 210 can allow for at least six-degree-of-freedom location determination.

The user 42 can position the alignment system 185 onto the patient 14 for a selected procedure. During positioning of the alignment device 185 onto the patient 14, the localizer array 210, within the patient support 212, can form a navigation field to assist in navigating the alignment device 185 onto the patient 14. Positioning the alignment device 185 onto the patient 14 can then be performed substantially precisely. The burr hole 164 can be formed before or after positioning the alignment device 185 on the patient 14 and navigating or guiding the alignment device 185 relative to the patient 14 can assist in ensuring an appropriate location of the alignment device 185 relative to the patient 14.

The alignment device 185 can be positioned on the patient 14 according to a plan or at predetermined location. As discussed above, the image data can be acquired of the patient 14 including the skull 60. The image data or any appropriate portion can be used to plan or predetermine the location for the alignment device 185. The navigation system 10 can, however, be used to navigate and track the position of the alignment device 185 relative to the patient 14, as discussed further herein. The position of the alignment device 185 can be displayed on the display 36 relative to the image data 38, which can include an image of the skull 60.

The alignment device 185 can include any appropriate alignment device 185, such as the Nexframe® alignment device 185. Other appropriate alignment device 185s 185, however, can be positioned relative to the patient 14 to achieve a selected position of the trajectory guide 232 relative to the patient 14.

The trajectory guide 232, however, can be positioned precisely relative to the patient 14 in a more efficient manner when the alignment device 185 is positioned at a selected location relative to the patient 14. For example, the trajectory guide 232 may be allowed to moved only through a range of motion, such as 30-60 degrees. Therefore, the 30-60 degrees of motion provides limits to the amount of trajectory of the instrument 187 can achieve relative to the patient 14 from any one location of the alignment device 185. Therefore, the trajectory guide 232, having the selected range of movement, can be positioned relative to the patient 14 to ensure an appropriate trajectory can be formed with the instrument 187.

Therefore, the localizer array 210 can be used to position the alignment device 185 relative to the patient 14. As discussed above, the localizer 210 can include one or more coils that can generate or sense a field. Thus, the various EM coils 234, 236, 238 on the alignment device 185 can act as tracking sensors, in concert with the localizer 210 during the positioning of the alignment device 185 relative to the patient 14.

Figure 10:
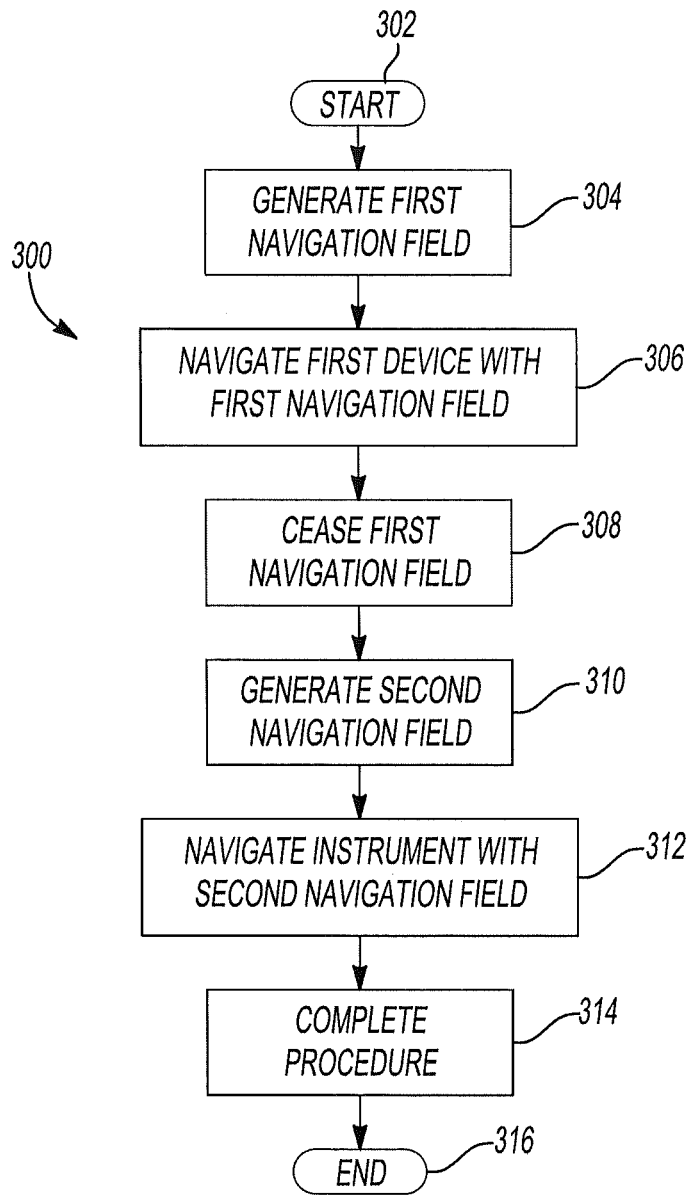
FIG. 10 is a flow chart of a method of performing a procedure, according to various embodiments.

The localizer 210 can create a first navigation or tracking field, as discussed further herein and illustrated in FIG. 10. The position of the EM coils 234, 236, 238 can be determined with the tracking system 46 using the first navigation field. The determined position of the alignment device 185 can be illustrated on the display 28 as icon or graphical representation 185'. Thus, the EM coils 234, 236, 238 can be tracked or the location of the coils can be determined with the tracking system 46 for determining the location of the alignment device 185.

The alignment device 185 can be fixed to the patient 14 in any appropriate manner. For example, one or more bone screws can be used to fix the alignment device 185 to the patient. Once fixed to the patient at least a portion of the alignment device 185 is substantially immovable relative to the patient 14. For example, the base 186 is substantially fixed relative to the patient 14 while the trajectory guide portion 232 may be able to move relative to the patient 14, at least during a selected portion of the procedure. Therefore, at least the EM coil 234 and the optional EM coil 236 are substantially fixed relative to the patient 14 once the base 186 of the alignment device 185 is fixed to the patient 14. The EM coils 234, 236, once the base 186 is fixed to the patient 14, can substantially define a dynamic reference frame or fixed EM coil relative to the patient 14.

If two coils are provided on the base 186, such as the first coil 234, and the second coil 236, the known position of the first coil 234 relative to the second coil 236 can be used to determine integrity of the field formed for navigation, such as the field defined by the localizer array 210. The integrity can include ensuring that a known position of the coils is being determined. If the determined position is different than a known or previous position it may indicate that there is an error or distortion in the generated field, such as interference from another metal object. It can also indicate that the instrument or device has been altered or damaged. Thus, integrity of the instruments or devices used in a procedure and the fields generated in the procedure an be checked or confirmed.

As discussed above, in an EM tracking system, the field provided by the localizer array 210 can include an electromagnetic field, which is measured or sensed by the EM coils 234, 236. Therefore, if a known relative location of the EM coils 234, 236 is known, the measured distance of the first EM coil 234 relative to the second coil 236 can be used by the workstation 28 to ensure an integrity of the field formed by the localizer array. It will be further understood, that a known position of the EM coil 238 on the trajectory guide 232 can also be used relative to either of the EM coils 234, 236 to determine integrity of the EM field.

In addition, the EM coils 234, 236, which are substantially fixed to the patient 14 due to their integration into the base 186, can also form a field relative to the instrument 187 and the trajectory guide EM coil 238. The field generated by the coils 234, 236, 238 of the alignment device 185 can generate a second navigation field, as discussed further herein and illustrated in FIG. 10. Therefore, the coils 234, 236 formed in the base 186 can also act as localizer coils, at least during a portion of a procedure relative to the patient 14. Because the EM coils 234, 236 are fixed relative to the patient 14, fields produced by the coils are also fixed relative to the patient 14. It will be understood, that the EM coils 234, 236 can be powered through any appropriate mechanism, such as a cable, a power signal, a power cell, or the like to produce a field that can be sensed with the coils 238, 240 on the trajectory guide 232 or the instrument 187, respectively.

During an operative procedure, the EM coil 240 on the instrument 187 can be used as a tracking sensor to determine the location of any portion of the instrument 187. In addition, the EM coil 238 on the trajectory guide 232 can be used to determine the trajectory or the position of the trajectory guide 232. It will be understood that the tracking sensors 240, 238 can be positioned at any appropriate location. For example, the tracking sensor 238 can be positioned substantially near or on an adapter 242 positioned in the trajectory guide 232.

The trajectory guide 232 can move relative to the base 186 via a track or slot 244, 246 defined by the trajectory guide 232. Thus, the trajectory guide 232 can be guided or navigated to a selected location or orientation relative to the burr hole 164 defined in the patient 14. The trajectory guide 232 can then be fixed in place via any appropriate mechanism, such as one or more locking screws 248, 250.

Once a trajectory is selected, the instrument 187 can be moved relative to the trajectory guide 232. Movement of the instrument 187 relative to the trajectory guide can be performed in any appropriate manner, such as via the user 42, a drive system 400 (FIGS. 8 and 11), a robot (either alone or incorporated with the drive system 400), or any other appropriate mechanism. Appropriate drive system 400 include the MICRODRIVE driving and positioning device sold by Medtronic, Inc. having a place of business in Colorado and Minnesota, USA. Regardless, the tracking sensor 240 of the instrument 187 can be tracked with a navigation field that can be created by various EM coils, such as the coils of the localizer 210 or the coils 234, 236 provided in the base 186.

The coils 234, 236 of the base 186 can be formed in the base as substantially a single piece. For example, the base 186 can be molded of plastic or polymer and the coils 234, 236 can be molded into the base 186. In addition, or alternatively, the coils 234, 236 can be welded, fixedly adhered, or any other appropriate mechanism can be used for fixing the coils 234, 236 to the base 186. The coils 234, 236, however, can be substantially fixedly positioned relative to the base 186. Regardless, the coils 234, 236 can be positioned on or in the base substantially directly so that a separate connection mechanism is not necessary or provided. Fixedly providing the coils 234, 236, either molded into or formed with the base, 186 can eliminate inadvertent movement of the coils 234, 236, inappropriate adjustments of the coils 234, 236, or operative time in positioning the coils 234, 236 on the base 186. It can also assist in properly navigating or guiding the base 186 relative to the patient 14 and also allow for use of the coils 234, 236 as localizing emitters.

In addition, the third EM coil 238 can be substantially integrated into the trajectory guide 232. The trajectory guide 232 can also be formed as a polymer or plastic material and the coil 238 can be molded with the trajectory guide 232 during formation of the trajectory guide 232. The integration or co-forming of the coil 238 and the trajectory guide 232 can also reduce inadvertent movement, incorrect attachments, and other issues with providing a separate or distinct EM coil from the trajectory guide 232.

The additional coil 240 can also be integrated or formed with the instrument 187 as one piece or member. The coil 240 can be used to determine a position and orientation or only a depth of the instrument 187. For example, once the trajectory portion 232 is fixed in a position the instrument 187 may only be able to move axially. Thus, its trajectory is known and its position along the axis can be determined and illustrated on the display 28.

Therefore, the EM coils 234, 236, 238 can be formed with the alignment device 185 to allow for a substantially rigid and fixed position of the EM coils 234, 236, 238 of the alignment device 185. In addition, the alignment device 185, therefore, can be navigated with a different localizer, such as the localizer 210, and then further define the navigation field for navigating the instrument 187 relative to the patient 14. The coils of the base 186 can be used to provide a navigation field at least, in part, because the position of the base 186 is known relative to the patient 14 due to navigating the base 186 relative to the patient 14 with the localizer 210. Therefore, the tracking system 46 is used to determine the position of the base 186 of the alignment device 185 to allow the EM coils 234, 236 to be used as localizer coils for a portion of the procedure, such as navigating the instrument 187 relative to the patient 14. It will be understood, however, that the localizer 210 can also be used in combination with the coils 234, 236 of the base for positioning or tracking other coils, such as the coils 238, 240 in the trajectory guide 238 and the instrument 187, respectively.

One skilled in the art will understand that the processes and systems discussed above can be used in a surgical procedure. The processes and systems, however, are understood to not be limited to use during or with a surgical procedure. The systems and processes can be used to acquire information regarding inanimate objects, inform or build a database of information; plan a procedure; formulate teaching aids, etc. Registration of image space to physical space can be performed relative to any object in physical space, including a patient, an inanimate object, etc. Also, the registration can occur for any appropriate reason, which may or may not be a surgical procedure.

With reference to FIG. 10, and FIGS. 8-9, the alignment device 185 can be positioned relative to the patient 14 and the instrument 187 can be guided relative to the patient 14, according to a method 300. The method 300 can start in start block 302. A first navigation field or localizer field can then be generated in block 304. A first device, such as the alignment device 185, can be navigated relative to the patient 14 using the first navigation field in block 306. As discussed above, for example, in relation to FIG. 8, the first navigation field can be formed with the localizer system 210. The localizer system 210 can be positioned substantially near the skull 60 of the patient 14 for producing a field generally in the area of navigating the alignment device 185 relative to the patient 14.

Once the first device has been navigated with the first navigation field, the first navigation field can be ceased in block 308. For example, once the alignment device 185 is mounted relative to the patient 14, the first navigation field can be ceased. If further portions or procedures are required, however, a second navigation field can be generated in block 310. As discussed above, the generation of the second navigation field can be formed with the EM coils 234, 236 associated with the base 186 of the alignment device 185. Therefore, the second navigation field can be generated with coils that are separate from the coils that generate the first navigation field in block 304.

The generation of the second navigation field can also include lower power or volume for various purposes. For example, the second navigation field can be generated to substantially include only a volume or area in which the instrument 187 can or is planned to be guided with the alignment device 185. It will also be understood that the coils may work in reverse to the above. For example, a first coil can sense a second field encompassing at least the head of the patient where a second coil generates the second field. The first coil can be positioned in or on the patient support, such as in the headrest, and the second coil can be associated with the alignment device 185, such as with integrated into the base of the alignment device 185. Accordingly, the navigation system 10 can be used to determine the location of a tracking device or coil if it is either generating a field that is sensed or sensing a field generated by another coil.

Therefore, the instrument 187 can be navigated with the second navigation field in block 312. The instrument 187 can be navigated in block 312 for any appropriate procedure, such as movement of an instrument into the skull 60 of the patient 14. Exemplary procedures include placement of the DBS, fixation of the lead, micro-recording, or the like.

The procedure can then be completed in block 314. The completion of the procedure in block 314 can include any appropriate steps or procedures, such as closing an incision, mounting a lead, or the like. The procedure method can then end in block 316. Therefore, it will be understood, that the procedure can allow for navigation of two or more instruments with two or more navigation fields. Moreover, the second navigation field can be generated after ceasing the first navigation field. Therefore, two different devices, such as the alignment device 185 and the instrument 187, can be navigated relative to the single patient 14 using two different navigation fields generated at two different times and by two different coils.

In addition, the two fields can be generated for various purposes. For example, the first navigation field can be generated to encompass substantially only the skull 60 of the patient 14. This can help reduce possible interference, reduce power, etc. for generating the field. The second navigation field can then be generated substantially only to encompass an area for navigation of the instrument 187. This, again, can help reduce interference in the field, etc. Thus, both of the navigation fields can be generated for various purposes and to achieve selected results, such as reduced interference, high field integrity, and navigational accuracy.

Also, the coils as a part of the alignment device 185 can provide further efficiencies. It can assist in the flow of the procedure by reducing system components and steps for performing a procedure. This can also streamline the piece-parts of the navigation system 10. The navigation system 10 including coils on the alignment device 185 can be used to reduce components and workflow for a procedure using the navigation system 10, as discussed above.

The various tracking systems (e.g. the EM tracking system 46 or the optical tacking system 46') of the navigation system 10, discussed above, can be used to track various tracking devices, as discussed above. For example, tracking devices can be associated with a subject and with instruments used during a procedure. The subject can include the patient 14 and the instruments can include a deep brain stimulation probe as the instrument 187, a drive system 400, and the alignment device 185. Tracking devices can be associated with numerous or all of the portions to track relative positions of all of these portions, including the patient, during a procedure.

Figure 11:
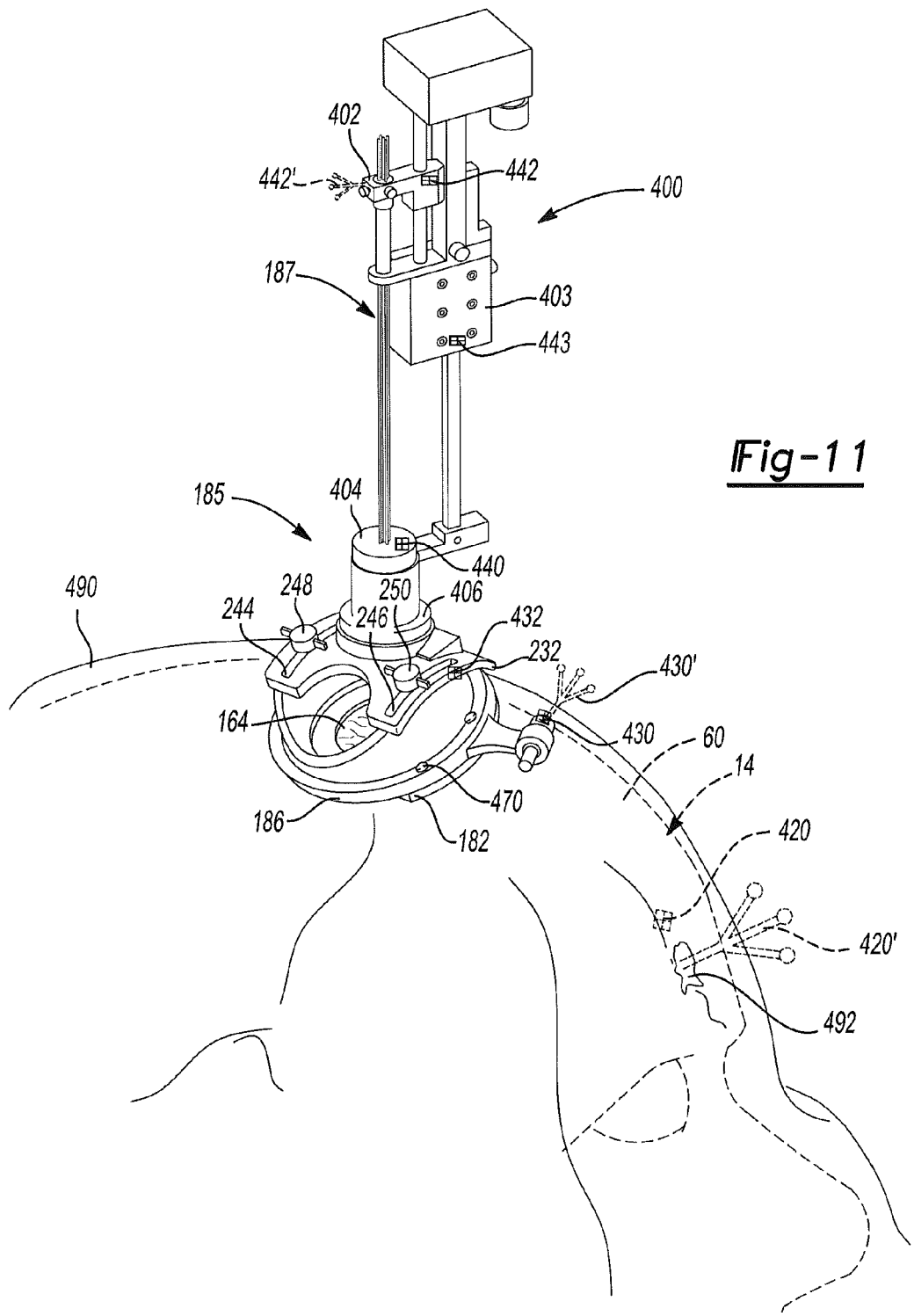
FIG. 11 is a schematic view of an alignment device and an instrument associated with a patient.

With reference to FIG. 11, the patient 14 can have the alignment system 185 positioned relative to the base 186 for an operative procedure. In the procedure, the instrument 187, which can include one or more electrodes or micro-electrodes, can be driven into the patient 14 with the drive system 400. The drive system 400 can include the MicroDrive system, discussed above. The drive system 400 can include various components, which can include an instrument pushing or mounting portion 402, an instrument guiding portion 404, and a drive mounting portion 406. The drive system 400, however, is connected to the alignment system 185 which can be fixed relative to the patient 14, as discussed above.

The alignment system 185 is affixed to the patient 14 with the base 186 and includes the trajectory guide portion 232 that can move relative to the base portion 186. The drive system 400 can be connected to the trajectory guide portion 232 and can move relative to the base 186 of the alignment system 185. Additionally, while the alignment system 185 is fixed relative to the patient 14, the alignment system 185 can also be moved relative to the patient 14 according to various embodiments.

Various portions of the alignment system 185 and the drive system 400 can be tracked and guided with the navigation system 10. The navigation system 10 can be used to track various tracking devices positioned relative to the patient 14 and other portions of the system within the navigational domain of the navigation system 10. One or more tracking systems, such as the EM tracking system 46 or the optical tracking system 46' can be provided with the navigation system 10. The various tracking systems 46, can be used to track and align the drive system 400 with the patient 14 and confirm or monitor the position of the drive system 400 relative to the patient 14. Further, the navigation system 10 can determine the position of the instrument 187 relative to the patient 14 either via direct navigation of the instrument 187 (e.g. a tracking device is incorporated with the instrument 187) or because the instrument 187 is fixed within the drive system 400 and the drive system 400 is tracked. Also, the alignment device 185, including the trajectory guide portion 232 can be tracked relative to the patient 14.

With continuing reference to FIG. 11, various tracking devices can be associated with the patient 14, the alignment system 185, and the drive system 400. According to various embodiments, an EM patient tracking device 420 can be fixed relative to the patient 14. As illustrated in FIG. 11, the EM patient tracking device 420 can be fixed to the scalp or skull 60 of the patient 14. It will be understood that an optical tracking device 420' can also be used with or alternatively to the EM patient tracking device 420. The tracking devices 420, 420' can be fixed to the patient 14 in any appropriate manner such as with bone screws, skin or bone adhesives, or other fixing mechanisms. Regardless, the patient tracking devices 420, 420' can be fixed relative to the patient 14 for tracking the patient 14 with the navigation system 10.

Additionally, the alignment system 185 can include one or more tracking devices. For example, a first alignment EM tracking device 430 can be interconnected with the alignment system 185, such as with a starburst connector. The tracking devices can also be integrated directly into or formed with any the alignment system 185 (e.g. molded into the alignment system 185). Alternatively, or in addition to the EM tracking device 430 an optical tracking device 430' can be interconnected with the alignment system 185. Generally, the first alignment system tracking devices 430, 430' can be interconnected with a portion of the alignment system 185 that is integrated with or rigidly connected to the base 186. Accordingly, a second alignment tracking device 432 can be associated or integrated connected with the trajectory guide portion 232. As discussed above, the trajectory guide portion 232 can move relative to the base 186. Accordingly, the second alignment system tracking device 432 can allow the trajectory guide portion 232 to be tracked independently and separately from the base 186.

The drive system 400 can also include one or more tracking devices. For example, a first drive system tracking device 440 can be integrated or connected with the drive system base 406. A second drive system tracking device 442 can be connected to a mobile or moveable portion of the drive system 402. Other portions, such as the upper or first alignment portion 403 can also include a tracking device, but one is not so required because the upper alignment portion can be fixed relative to the base 404. Connecting or associating a tracking device 443 with the support alignment portion 403 can assist in determining motion of the drive system relative to the patient 14 as the upper portion can be selected to be unmoved during a procedure.

Any of the tracking devices 440, 442, 443 can be any appropriate tracking device, such as the EM tracking device, optical tracking device, acoustic tracking device, etc. As discussed above, the device holding portion 402 can move relative to the drive system base 406 during a procedure of driving the instruments 187 into the patient 14. Thus, the second drive system tracking device 442 can be connected to the instrument engaging portion 402. In addition, it will be understood that any of the drive system tracking devices 440 or 442 can include optional or alternative optical tracking devices 442'. In addition, any of the portions of the drive system 400 can include tracking devices in addition to the fixed base or alignment portion 404 or the moveable portion 402.

As illustrated in FIG. 11, various tracking devices can be associated and connected to the patient 14, the alignment system 185, the drive system 400, and/or the instrument 187. The various tracking devices allow various and selected portions of the alignment system and the drive system 185, 400 respectively, to be tracked relative to the patient 14 together or independently of one another. As discussed below, it will generally be understood that tracking an instrument can include tracking any or all of the alignment system 185, the drive system 400, the instruments 187 associated with the patient 14.

Figure 12:
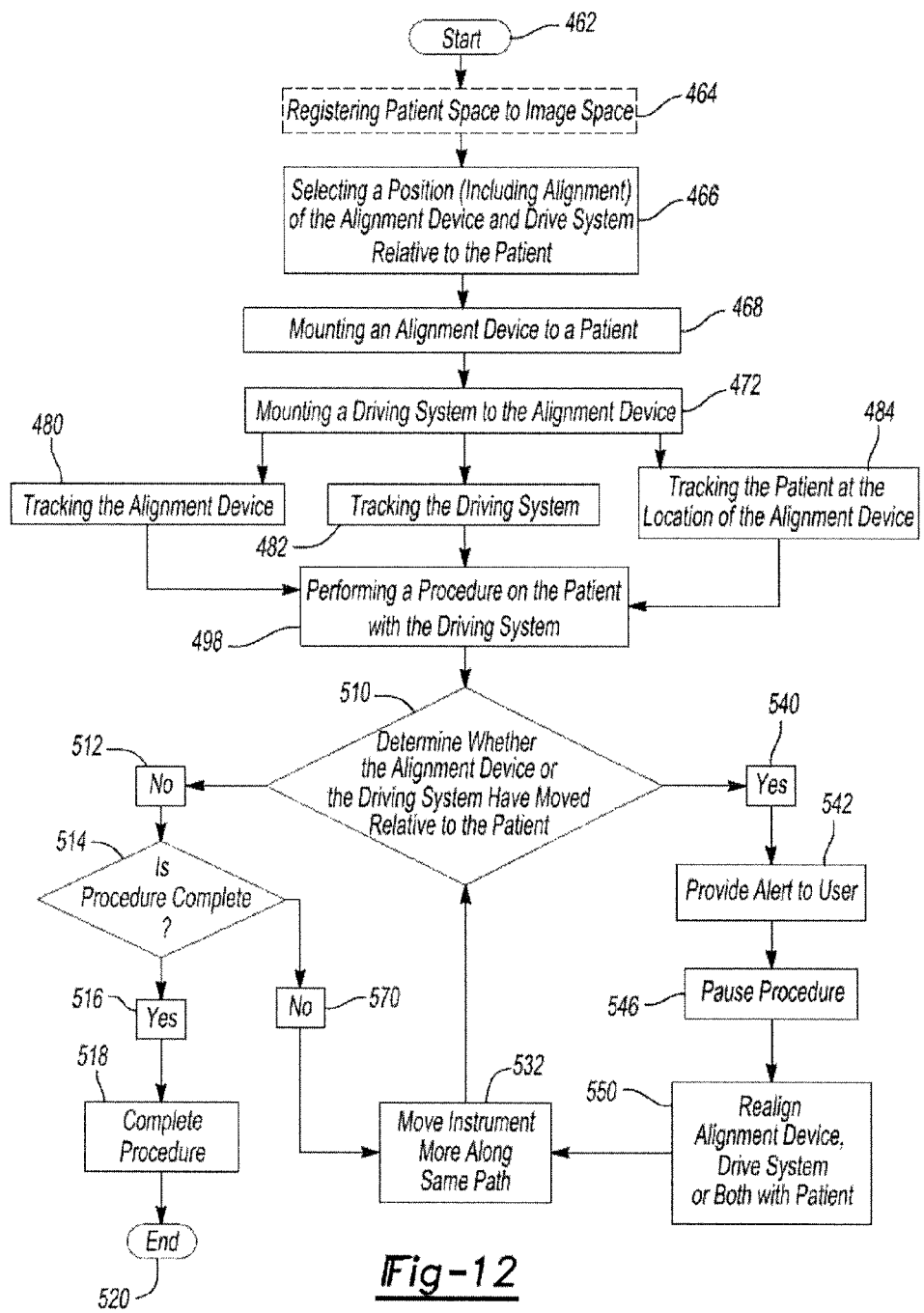
FIG. 12 is a flow chart illustrating a method of performing a procedure.

With additional reference to FIG. 12, a flow chart 460 illustrates a method of performing a procedure using the multiple tracking devices discussed above. Generally, the method of the flow chart 460 can begin in start block 462 to start the procedure. The procedure can include optionally registering the patient 14 to image data acquired of the patient 14. As discussed above, the imaging system 16 can acquire image data of the patient 14. It will be further understood, that any appropriate imaging system can acquire any appropriate image data of the patient 14. For example, magnetic resonance image data (MRI), computer tomography (CT) image data, or other appropriate types of image data can be acquired of the patient 14. Other image data can also be used to reconstruct or form an image, such as a 3D image of the patient. Other image data can include single photon emission computed tomography (SPECT) or Diffusion Tensor Imaging (DTI). The acquired image data can define image space that relates to the patient 14. During registration, as discussed above, the physical space defined by and relative to the patient 14 can be registered to the image space defined by the image data. In registering the patient 14 to the image space, the physical space that is navigated with a navigation system 10 can be registered to the image data to illustrate or determine a position of a tracked instrument or a portion in the patient space relative to the image data. It will be understood that registering patient space to the image space in block 464 is optional, as discussed further herein. Nevertheless, to permit illustration of the position of a tracked instrument relative to the image data, registration generally occurs. To determine whether any of the instruments have moved relative to the patient 14, however, registration is not required and only tracking the instrument and the patient 14 can be used to make the determination. Tracking can be in real time, such as during a procedure and substantially continuously.

After the optional registration of the patient space to the image space in block 464, a selection of a position (including physical location and alignment) of the alignment device 185 and the drive system 400 relative to the patient 14 or selected target within the patient 14 can be performed in block 466. Selecting the alignment of the alignment system 185 and/or the drive 400 relative to the patient 14 can include planning a procedure after viewing image data or selecting a trajectory to position the instrument 187 relative to a selected portion of the patient 14. For example, according to various embodiments, the instrument 187 can include deep brain stimulation (DBS) probes that are driven into the brain of the patient 14. Accordingly, the alignment of the drive 400 can determine the position of the instruments 187 after implantation. Selecting the appropriate position and alignment is understood by one skilled in the art, and will not be discussed in detail here.

After selecting the appropriate position, the alignment device 185 can be mounted on the patient in block 468. Mounting the alignment device 185 to the patient 14 can include a mounting the alignment device 185 in any appropriate manner. For example, as discussed above, the alignment device 185 can include or be the NEXFRAME® alignment system sold by Medtronic, Inc. Various mechanisms, such as fixation screws or pins 470 can be used to fix the alignment system 185 to the patient 14. The screws or pins can pass through a portion of the alignment system 185, such as the base 186, to hold the alignment system 185 to the skull 60 of the patient 14. The alignment system 185 is generally positioned over the burr hole 164 formed in the skull 60 of the patient 14.

Once the alignment device 185 is positioned relative to the patient 14 at the selected position, the drive system 400 can be mounted to the alignment device 185 in block 472. Mounting the drive system 400 to the alignment device 185 can also be performed in any appropriate manner. For example, the mounting or base portion 406 of the drive system 400 can be positioned and fixed relative to the trajectory guide portion 232 of the alignment system 185. For example, the base portion 406 can be threaded or can be adhered to the trajectory guide portion 232 of the alignment system 185. Generally, the drive system 400 can include a MicroDrive, sold by Medtronic, Inc. and the alignment system 185 can be the NEXFRAME® and both can be connected in a commonly known manner.

Once the drive system 400 and the alignment device or system 185 is mounted or fixed relative to the patient 14, the navigation system 10 including the tracking systems 46, 46' can be used to track the various tracking devices affixed to the patient 14, including those associated with the alignment system 185, and the drive system 400. In particular, after mounting the drive system 400 on the alignment device 185 in block 462, the alignment device 185 can be tracked in block 480. The drive system 400 can be tracked in block 482. The patient can be tracked in block 484.

Tracking each of the alignment device 185, driving system 400, and the patient 14 can be done with the various tracking devices discussed above. For example, the patient tracking devices 420, 420' can be affixed to the patient 14. Similarly, the alignment device tracking devices 430, 430', and 432 can be affixed or integrated with the alignment system 185. Further, the drive tracking devices 440, 442 and 442' can be integrated or interconnected with the drive system 400. The various tracking devices can be tracked by the respective tracking systems 46, 46' depending upon the type of tracking device that is associated with the patient 14, the alignment system 185, or the drive system 400.

The tracking system can further assure that the instruments 187 will be maintained or are maintained on a selected trajectory. Generally, the base 186 is positioned over the burr-hole 164 such that the instruments 187 will pass through a brain or other anatomical target. The drive system 400 can then be attached to the base to drive the instruments into the anatomy to the target. By tracking the base 186, the drive system 400, and other parts of the system relative to the patient 14 it can be determined if any part has moved relative to another part.

It will be understood that any appropriate tracking system can be used and the tracking devices associated with the patient 14, the alignment system 185, and the drive system 400 can be selected based upon the appropriate tracking system. In addition, tracking systems other than optical or EM tracking systems can be used. For example, an accelerometer, acoustic, radar, and other appropriate tracking systems can be used to track the patient 14, the alignment system 185, or the drive system 400.

The tracking devices and the relative position of the patient 14, the alignment system 185, or the drive system 400 can all be tracked and determined during the surgical procedure. Even if the patient 14 is covered in a drape 490. The patient tracking devices 420' can be mounted to extend through the drape 490 such as via a puncture 492 through the drape 490. It will be understood that the EM patient tracking device 420 is not required to have line of sight and can be covered with the drape 490. In addition, portions of the drive 400, the alignment system 185, or other portions might be covered with a drape or other sterile portions and accordingly, the tracking devices can include stems or bases to extend to be viewed with the localizers, such as the optical localizer 46'.

While tracking each of the alignment device 185, the drive system 400 and the patient in blocks 180, 182, 484, a procedure can be performed on the patient 14, such as driving the instruments 187 into the patient 14 with the drive system 400, in block 498. Driving the instruments 187 into the patient 14 with the drive system 400 can be performed with a mechanical drive, that can be manually operated or powered. The drive system 400 can be operated in a manual manner to move the instrument moving portion 402 relative to the base 406. The drive tracking devices 442, 442' can be used to track the position of the drive system 400 in the patient space. Additionally, the patient tracking devices 420, 420' can be used to track the position of the patient 14 in the patient space. It can be selectively chosen to illustrate an instrument icon 187*i* representing a location of the instrument 187 relative to the image data of the patient 14 on the display device 36.

Figure 13A:
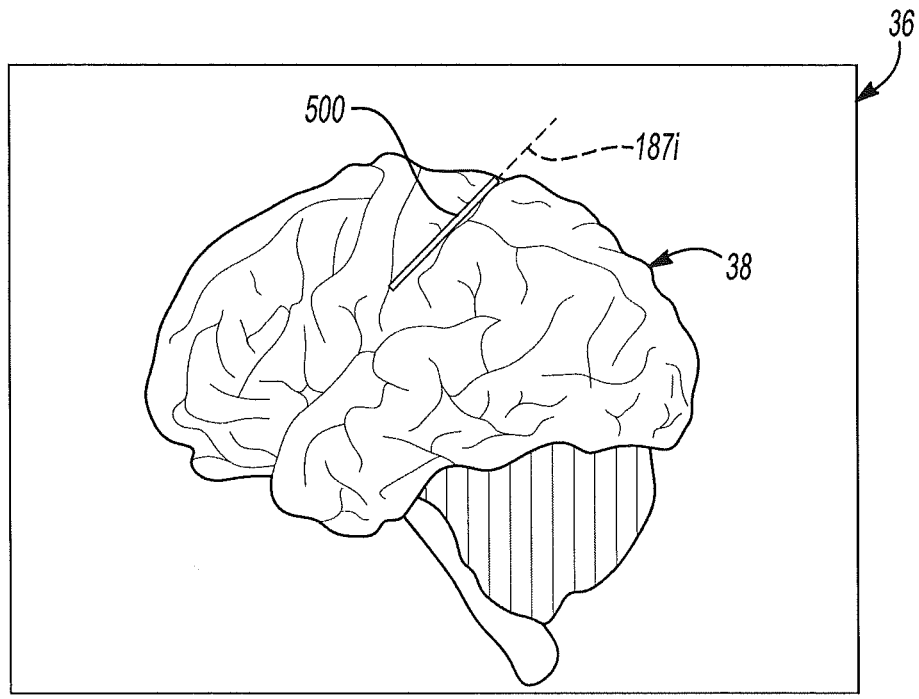
FIG. 13A is a view of a display device illustrating an output of a navigation system determination of a position of an instrument.

With additional reference to FIG. 13A, the display device 36 can display the image 38 generated from the image data and a planned trajectory icon 500. A tracked position of the instrument can be illustrated as the icon 187' relative to the image 38 and the planned trajectory 500. As illustrated in FIG. 13A, the tracking of the drive system 400 and the alignment system 185 relative to the patient 14 can be used to illustrate that the instrument 187 is in alignment with a planned trajectory 500. The planned trajectory 500 can include information that relates to the selected position alignment of the drive system 400 and the alignment system 185 relative to the patient 14 determined in block 466.

A determination of whether the alignment device 185 or drive system 400 has moved relative to the patient can then be made in block 510. By tracking all of the patient 14, the alignment system 185, and the drive system 400 the determination can be made as to whether any of these have moved relative to one another. If the determination is NO in block 512, a second determination of whether the procedure is complete in block 514 can be made. If it is determined that the procedure is complete in block 514, then the path through the YES block 516 can be followed and the procedure can be completed in block 518. Completing the procedure can include removing all of the portions affixed to the patient, including the patient tracking devices 420, 420' the alignment system 185 and the drive system 400. Additionally, other portions of the procedure can be performed including locking the instruments 187 in place, closing the incision, and other generally known procedure completion practices. The entire method can then end in block 520.

If it is determined that the procedure is not complete in block 514, the path through the NO block 570 can be followed and the instrument 187 can be continued to be moved along the same alignment and location of the drive system 400 and the alignment system 185 in block 532. It can then again be queried as to whether the alignment device 185 or the drive system 400 has moved in block 510. The procedure can then follow the NO path 512 until the YES determination in block 516 of the completed procedure has been reached.

It will be understood that querying the determination of whether the alignment device 185 or the drive system 400 have moved in block 510 can happen at any appropriate interval. For example, the drive system 400 can be moved at a steady or continuous rate. The system can make a determination of whether the alignment system 185 or the drive system 400 has moved at a selected time or interval. Generally, the system can indicate immediately, or as soon as possible, after a particular motion has occurred that such a motion has occurred. For example, an undesirable motion can be indicated immediately or as soon as the system can cycle to check for motion again.

Additionally, the determination of movement of the drive system 400 or the alignment system 185 can be made based on intervals of movement of the instrument by the drive system 400. For example, a query can occur after each one millimeter of axial movement of the instruments 187 with the drive system 400 or at any appropriate time interval or distance interval. Additionally, the query can be made if the tracking system detects a selected amount or threshold of movement of any of the tracked portions. Large or small intervals can be selected, or it can be selected to be substantially continuous or real time query for movement.

Figure 13B:
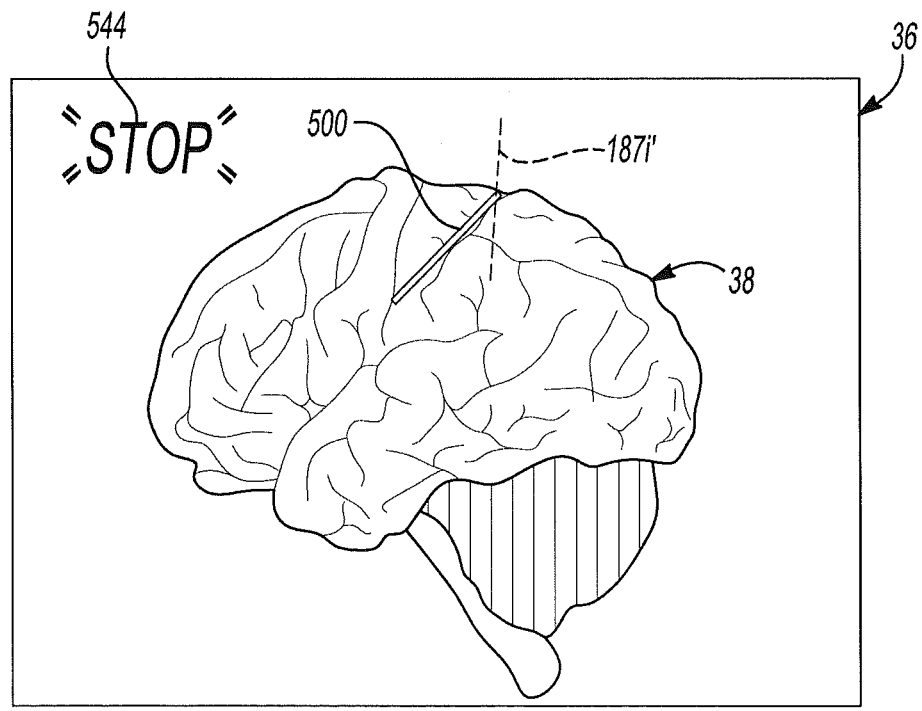
FIG. 13B is a view of a display device providing an output regarding a determined position of an instrument relative to a selected position.

If the determination is that movement has occurred from the selected position in block 510, the determination of YES can be made in block 540. When it has been determined that the drive system 400 of the alignment system 185 has been moved from the selected position in block 466, an alert to the user can be provided in block 542. As illustrated in FIG. 13B, when the alignment is improper an icon 187*i*' can illustrate that the position of the instrument 187 is not aligned with the planned path 500. In such a case, an optical or visual indication that the procedure should stop or an error has occurred can include a STOP icon 544 on the display device 36. It will be further understood that any appropriate alert maybe provided to the user 42, such as the display device 36 flashing (e.g. cycling quickly through multiple colors), an auditory signal, a tactile signal, or other appropriate signals. For example, the display device 36 may go blank and no longer indicate a tracked position of the patient 14, instruments 187, drive device 400, or alignment device 185 relative to the patient 14.

After the alert is sounded, the procedure can be paused in block 546. After pausing the procedure, and after appropriate preparation, such as possibly withdrawing the instruments 187 from the patient 14, realignment of the alignment system 185, drive system 400, instruments 187, or other appropriate portions relative to the patient 14 can occur in block 550. Re-aligning any of the drive system 400 or the alignment system 185 relative to the patient 14 can include realigning the various portions to the selected position in block 466. Once the realignment has occurred, the instrument can be further moved along the selected path in block 532. The iterative process of determining whether the alignment system 185 or the drive system 400 is moved can then occur until the procedure is completed in block 518.

Accordingly, the procedure in the flow chart 460 can be used to determine whether the drive system 400 or the alignment system 185 has moved from a selected position relative to the patient 14. The tracking devices affixed to the patient 14 and other portions being moved relative to the patient 14, including the alignment device 185, the drive system 400, or even the instruments 187 themselves can be used to determine or track a position of each of these portions relative to the patient 14. It will be understood, however, that the selected position in block 466 can be any absolute or relative position and a determination of whether any appropriate relative or absolute position has occurred. Thus, the determined relative motion need not be relative to the patient 14.

The procedure in the flowchart 460 can be included as an algorithm and software executed by the navigation system 10 and can then be used to determine whether any of the portions have moved (e.g. relative to the patient 14) during a procedure being performed on the patient 14. It will be understood that any appropriate procedure can occur and any appropriate tracking devices can be associated with the patient 14 during the procedure. Accordingly, although the individual or small tracking devise 420, 420' are illustrated relative to the patient 14, any of the tracking systems or tracking devices discussed above can also be used as tracking devices associated with the patient 14 or any other appropriate portion of the system described herein.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A system to track and determine a location of an instrument relative to a subject, comprising:
   an alignment system including an alignment base configured to be fixed directly to the subject with a fixing member and a trajectory portion operable to selectively move relative to the alignment base and be fixed relative to the alignment base, wherein the trajectory portion has at least two slots therethrough to allow movement of the trajectory portion relative to the alignment base;
   a drive system supported by the alignment system and configured to drive the instrument into the subject, wherein the drive system has an instrument engaging portion and a drive base to be connected directly to the trajectory portion, wherein the instrument engaging portion is moveable relative to the drive base that is connected to the trajectory portion;
   a subject tracking device configured to be connected directly to the subject separate and spaced apart from the alignment system;
   a drive system tracking device connected to the drive system having at least a first tracking device portion and an alignment system tracking device connected to the alignment system having at least a second tracking device portion; and
   a tracking system configured to track the subject tracking device, the alignment system tracking device, and the drive system tracking device.

2. The system of claim 1,
   wherein the drive system tracking device further includes at least the first tracking device portion connected to the drive base and a third tracking device portion connected to the instrument engaging portion configured to allow tracking of the drive base relative to the instrument engaging portion.

3. The system of claim 2, further comprising:
   a display device operable to display the tracked position of at least one of the alignment base and the drive system relative to the subject.

4. The system of claim 3, wherein the display device is operable to further display a selected position of at least one of the alignment system and drive system relative to the subject and further operable to display an indication of whether at least one of the alignment system and the drive system are at the selected position relative to the subject.

5. The system of claim 1, further comprising:
   a navigation processor operable to execute instructions to determine a relative position of the subject tracking device and the drive system tracking device and generate an output signal based upon the determined relative position of the subject tracking device and the drive system tracking device.

6. The system of claim 5, wherein the alignment system tracking device is connected directly to the alignment system when the drive system tracking device is connected directly to the drive system;
   wherein the tracking system is further operable to simultaneously track the alignment system tracking device with the subject tracking device and the drive system tracking device;
   wherein the navigation processor is operable to output a signal based upon a determined relative position of all of the subject tracking device, the drive system tracking device, and the alignment system tracking device.

7. The system of claim 6, wherein the tracking system includes at least one of an electromagnetic tracking system, an optical tracking system, an acoustic tracking system, and combinations thereof.

8. The system of claim 1, further comprising:
   a signal emitting system operable to emit a signal to a user regarding the relative location of the alignment system and the drive system relative to the subject and provide a signal regarding if either of the alignment system or the drive system are at an unselected position relative to the subject.

9. The system of claim 1, wherein the tracking system includes an electromagnetic localizer;
   wherein the alignment system tracking device is operable as the electromagnetic localizer to at least emit an electromagnetic field sensed by at least the drive system tracking device and a navigation processor is configured to determine a location of the drive system tracking device based thereon.

10. A system to track and determine a location of an instrument relative to a subject, comprising:
    an alignment system operable to be connected to the subject having a trajectory portion operable to be moved relative to the subject at an alignment device selected position and a fixing portion operable to fix the trajectory portion relative to the subject, wherein the trajectory portion has at least two slots therethrough configured to allow movement of the trajectory portion relative to the subject;
    a drive system configured to be placed at a drive system selected position and to drive the instrument into the subject, wherein the drive system has a drive base to be connected to the trajectory portion, wherein the instrument is moveable relative to the drive base that is connected to the trajectory portion;

a subject tracking device configured to be connected directly to the subject separate and spaced apart from the alignment system;

a drive system tracking device connected to at least one of the alignment system and the drive system;

a tracking system to track the subject tracking device and the drive system tracking device; and a navigation processor at least configured to:

determine whether either of the alignment device or the drive system have moved from either of the alignment device selected position and drive system selected position while moving the instrument into the subject with the drive system and while guiding the instrument with the alignment device at least by tracking the subject tracking device relative to the drive system tracking device, generate an icon to illustrate a tracked position of the instrument relative to an icon of a planned path, and output an alert signal if it is determined that either of the alignment device or the drive system has moved from the respective selected positions relative to the subject tracking device.

11. The system of claim 10, further comprising:
at least one of a micro-electrode or deep brain stimulation probe as the instrument.

12. The system of claim 10, wherein the navigation processor configured to determine whether the alignment device and the drive system have moved includes determining whether the alignment system or the drive system has moved after a time selected interval.

13. The system of claim 10, further comprising:
a display device operable to display an image representative of the subject;
wherein the navigation processor is further configured to determine a position for a display of an icon representing a position of at least one of the drive system or the instrument relative to the displayed image of the subject.

14. The system of claim 13, wherein the navigation processor includes a plurality of processors.

15. The system of claim 13, wherein output a signal includes displaying on the display device a selected position of at least one of the drive system, the alignment device, and the instrument relative to a representation of a pre-selected position of at least one of the respective drive system, alignment device, or an instrument selected position of the instrument.

16. The system of claim 10, further comprising:
an alignment system tracking device;
wherein the alignment system tracking device and the drive system tracking device are both electromagnetic tracking devices.

17. The system of claim 16, wherein the tracking system is an electromagnetic tracking system and the first coil is an electromagnetic localizer.

18. The system of claim 17, wherein the alignment system tracking device is operable as the electromagnetic localizer to at least emit the electromagnetic field sensed by at least the drive system tracking device and the navigation processor is configured to determine a location of the drive system tracking device based thereon.

19. The system of claim 16, wherein the alignment system includes a trajectory guide configured to move relative to a base and the alignment system tracking device is fixed to the trajectory guide.

20. The system of claim 10, wherein the navigation processor is configured to make a determination of a relative position of at least one of the alignment device, the drive system, or the instrument relative to the subject at least by tracking the subject tracking device.

21. A system to track and determine a location of an instrument relative to a subject, comprising:

an alignment device having at least a base configured to be fixed directly to the subject at a first selected position and a trajectory guide configured to move relative to the base via a first slot and a second slot extending through the trajectory guide, wherein the alignment device is operable to align the instrument relative to the subject for a selected procedure to be performed on the subject;

a drive system connected at a second selected position relative to the alignment device to drive the instrument into the subject for performing the selected procedure on the subject;

a tracking system including:
an alignment tracking device fixed to the alignment device, wherein the alignment tracking device is operable to allow tracking the alignment device;
a drive system tracking device affixed to the drive system; and
a subject tracking device configured to be connected directly to the subject spaced apart and separate from the alignment device to allow tracking of the subject;
wherein the tracking system is configured to generate a tracking signal regarding a tracked location of at least one of the alignment tracking device, the drive system tracking device, or the subject tracking device; and a navigation processor configured to, with the generated tracking signal:
determine whether either of the alignment device or the drive system have moved from either of the first selected position or the second selected position while moving the instrument into the subject with the drive system and while guiding the instrument with the alignment device; and
output a signal if it is determined that either of the alignment device or the drive system has moved from the respective selected positions.

22. The system of claim 21,
wherein the alignment tracking device is fixed to the trajectory guide;
wherein the base is configured to contact the subject only near the portal and the subject tracking device is spaced away from the base.

23. The system of claim 21, further comprising:
a display device configured to display at least two of a position of the subject, the alignment device, the drive system, or the instrument to illustrate a relative position between the displayed at least two of the subject, the alignment device, the drive system, or the instrument.

24. The system of claim 23, wherein the determination of whether either of the alignment device or the drive system has moved from either of the first selected position or second selected position, the determination is based on an absolute respective selected positions and the determination is not made on movement of the alignment device or the drive system relative to the subject tracking device.

25. The system of claim 23, wherein the determination of whether either of the alignment device or the drive system has moved from either of the first selected position or second selected position, the determination is based on movement of the alignment device or the drive system relative to the subject tracking device.

26. The system of claim 21, wherein the tracking system further includes an electromagnetic localizer configured to emit an electromagnetic field, wherein the subject tracking device is configured to be selectively operated as the electromagnetic localizer to at least emit the electromagnetic field operable to track the alignment tracking device and the drive system tracking device by each sensing the electromagnetic field;
   wherein the tracking signal regarding the tracked location generated by the tracking system is based on the sensing of the electromagnetic field.

* * * * *